(12) United States Patent
Phillips et al.

(10) Patent No.: US 7,157,436 B2
(45) Date of Patent: Jan. 2, 2007

(54) THERAPEUTICALLY USEFUL SYNTHETIC OLIGONUCLEOTIDES

(75) Inventors: Nigel C. Phillips, Point-Claire (CA); Mario C. Filion, Laval (CA)

(73) Assignee: Bioniche Life Sciences, Inc., Pointe-Claire (CA)

( * ) Notice: Subject to any disclaimer, the term of this patent is extended or adjusted under 35 U.S.C. 154(b) by 0 days.

(21) Appl. No.: 09/735,363

(22) Filed: Dec. 12, 2000

(65) Prior Publication Data

US 2001/0041681 A1    Nov. 15, 2001

Related U.S. Application Data

(60) Provisional application No. 60/228,925, filed on Aug. 29, 2000, provisional application No. 60/170,325, filed on Dec. 13, 1999.

(51) Int. Cl.
| | |
|---|---|
| A01N 43/04 | (2006.01) |
| A01N 61/00 | (2006.01) |
| C12N 15/63 | (2006.01) |
| C07H 21/04 | (2006.01) |
| A61K 49/00 | (2006.01) |

(52) U.S. Cl. .................... 514/44; 424/9.1; 424/9.2; 435/6; 435/91.1; 435/455; 514/1; 514/2; 536/23.1; 536/24.1; 536/24.33

(58) Field of Classification Search .................... 435/6, 435/91.1, 455, 91.31, 458; 536/23.1, 24.5, 536/24.1, 24.3, 24.33; 514/1, 4, 44, 2; 424/9.1, 424/9.2; 530/300, 350
See application file for complete search history.

(56) References Cited

U.S. PATENT DOCUMENTS

| | | | |
|---|---|---|---|
| 4,983,518 A | | 1/1991 | Schaffner et al. |
| 5,474,796 A | * | 12/1995 | Brennan .................... 427/2.13 |
| 5,582,981 A | * | 12/1996 | Toole et al. .................... 435/6 |
| 5,861,245 A | * | 1/1999 | McClelland et al. ........... 435/6 |
| 6,211,431 B1 | * | 4/2001 | Boevink et al. ............ 800/278 |
| 6,255,473 B1 | * | 7/2001 | Vitek et al. ................. 536/24.1 |

FOREIGN PATENT DOCUMENTS

| | | | |
|---|---|---|---|
| WO | WO 94 08053 A | | 4/1994 |
| WO | WO 96 23508 A | | 8/1996 |
| WO | WO 96/39500 | * | 12/1996 |
| WO | WO 97 20924 A | | 6/1997 |
| WO | WO 97/20924 A1 | | 6/1997 |

OTHER PUBLICATIONS

Promega Catalogue (1998).*
Boehringer Mannheim Catalogue (1997).*
Peracchi, A., Rev. Med. Virol., vol. 14, pp. 47-64 (2004).*
Chirila, T.V. et al., Biomaterials, vol. 23, pp. 321-342 (2002).*
Branch, A., Trends in Biochem. Sci., vol. 23, pp. 45-50 (1998).*
Agrawal, S. et al., Molecular Med. Today, vol. 6, pp. 72-81 (2002).*
Crooke, S.T., antisense Research and Application, Chapter 1, pp. 1-50, Ed. by S. Crooke, Publ. by Springer-Verlag (1998).*
Bates et al., "Antiproliferative Activity of G-rich Oligonucleotides Correlates with Protein Binding," The Journal of Biological Chemistry, vol. 274, No. 37, Sep. 10, 1999, pp. 26369-26377.
Morassutti et al., "Nucleosides & Nucleotides," 18(6&7), pp. 1711-1716 (1999).
Scaggiante et al., "Human cancer cells lines growth inhibition by $GT_n$ oligodeoxyribonucleotides recognizing single-stranded DNA-binding proteins," European Journal of Biochemistry, vol. 252, pp. 207-215, 1998.
Ballas et al., "Induction of NK Activity in Murine and Human Cells by CpG Motifs in Oligodeoxynucleotides and Bacterial DNA," J. Immunol., Sep. 1, 1996, p. 1840-1845, vol. 157.
Bates et al., "Antiproliferative Activity of G-rich Oligonucleotides Correlates with Protein Binding," J. Biol. Chem., Sep. 10, 1999, vol. 274, pp. 26369-26377.
Braun et al., "Cytotoxic T Cells Deficient in Both Functional Fas Ligand and Perforin Show Residual Cytolytic Activity yet Lose Their Capacity to Induce Lethal Acute Graft-Versus-Host Disease," J. Exp. Med., 1996, p. 657-661, vol. 183.
Famularo et al., "Fas/Fas Ligand on the Road; An Apoptotic Pathway Common to AIDS, Autoimmunity, Lymphoproliferation and Transplantation," Med. Hypoth.,.1999, p. 50-62, vol. 53.
Filion, M.C. et al., "Inhibition of cell cycle progression and induction of apoptosis in leukemia cells by *Mycobacterium phlei* DNA and derived synthetic oligonucleotides." Clinical Cancer Research (Nov. 7-10, 2000), vol. 6, Supp.; p. 4571S.
Filion, M.C. et al., "*Mycobacterium phlei* cell wall complex directly induces apoptosis in human bladder cancer cells." British Journal of Cancer (Jan. 1999) 79(2) 229-35.
Filion, M.C., et al., "Modulation of interleukin-12 synthesis by DNA lacking the CpG motif and present in a mycobacterial cell wall complex." Cancer Immunology Immunotherapy (Aug. 2000), 49(6), pp. 325-334.
Griffith, et al., "Fas Ligand-Induced Apoptosis as a Mechanism of Immune Privilege," Science, Nov. 17, 1995, vol. 270, pp. 1189-1192.
Hochhauser, D., "Modulation of chemosensitivity through altered expression of cell cycle regulatory genes in cancer," Anti-Cancer Drugs, 1997, vol. 8, pp. 903-910.

(Continued)

Primary Examiner—Jane Zara
(74) Attorney, Agent, or Firm—Kilpatrick Stockton LLP

(57) ABSTRACT

The present invention provides a composition and method comprising a 2–20 base 3'-OH, 5'-OH synthetic oligonucleotide (sequence) selected from the group consisting of $(G_xT_y)_n$, $(T_yG_x)_n$, $a(G_xT_y)_n$, $a(T_yG_x)_n$, $(G_xT_y)_nb$, $(T_yG_x)_nb$, $a(G_xT_y)_nb$, $a(T_yG_x)_nb$, wherein x and y is an integer between 1 and 7, n is an integer between 1 and 12, a and b are one or more As, Cs, Gs or Ts and wherein the sequence induces a response selected from the group consisting of induction of cell cycle arrest, inhibition of proliferation, activation of caspases and induction of apoptosis in cancer cells and production of cytokines by immune system cells.

23 Claims, 3 Drawing Sheets

OTHER PUBLICATIONS

Klinman et al., "CpG Motifs Present in Bacterial DNA Rapidly Induce Lymphocytes to Secrete Interleukin 6, Interleukin 12, and Interferon γ," Proc. Natl. Acad. Sci. USA, Apr. 1996, pp. 2879-2883, vol. 93.

Kondo et al., "Essential Roles of the Fas Ligand in the Development of Hepatitis," Nature Med., Apr. 1997, pp. 409-413, vol. 3, No. 4.

Lipford et al., "CpG-Containing Synthetic Oligonucleotides Promote B and Cytotoxic T Cell Responses to Protein Antigen: A New Class of Vaccine Adjuvants," Eur. J. Immunol., 1997, pp. 2340-2344, vol. 27.

Morassutti, et al., "Correlation between cytotoxic effect and binding to nuclear proteins of oligomeric d(GT)n sequences in human cancer CCRF-CEM cell line," Minerva Biotec, Jun. 1995, pp. 176-181.

Morassutti, et al., "Effect of Oligomer Length and Base Substitutions On The Cytotoxic Activity and Specific Nucelar Protein Recognition of GTn Oligonucleotides in the Human Leukemic CCRF-CEM Cell Line," Nucleosides and Nucleotides, 18(6&7), pp. 1711-1716 (1999).

Nagata, S., "Fas Ligand-Induced Apoptosis," Ann. Rev. Genet., 1999, pp. 29-55, vol. 33.

Nishioka et al., "An Augmentation of Fas (CD95/APO-1) Antigen Induced by Radiation: Flow Cytometry Analysis of Lymphoma and Leukemia Cell Lines," Int. J. Mol. Med., 1999, pp. 275-278, vol. 3.

O'Connell, et al., "The Fas Counterattack: Fas-Mediated T Cell Killing by Colon Cancer Cells Expressing Fas Ligand," J. Exp. Med., Sep. 1996, pp. 1075-1082, vol. 184.

Owen-Schaub et al., "Fas and Fas Ligand Interactions in Malignant Disease (Review)," Int. J. Oncol., 2000, pp. 5-12, vol. 17.

Promega Catalog 1993/94, Revolutions in Science, cover and pp. 90-91.

Reader, S., et al., "Identification of non-antisense phosphodiester oligonucleotides that induce cell cycle arrest and apoptosis in cancer cells." Clinical Cancer Research (Nov. 7-10, 2000), vol. 6, Supp.; p. 4571S.

Sabelko-Downes et al., "The Role of Fas Ligand *in vivo* as a Cause and Regulator of Pathogenesis," Curr. Opin. Immunol., Jun. 2000, pp. 330-335, vol. 12.

Scaggiante et al., "Human Cancer Cell Lines Growth Inhibition by $GT_n$ Oligodeoxyribonucleotides Recognizing Single-Stranded DNA-Binding Proteins," Eur. J. Biochem., Mar. 1, 1998, pp. 207-215, vol. 252.

Sheard et al., "UP-Regulation of FAS (CD95) in Human $p53^{wild-type}$ Cancer Cells Treated With Ionizing Radiation," Int. J. Cancer, Nov. 27, 1997, pp. 757-762, vol. 73.

Vlassov et al., "Transport of Oligonucleotides across Natural and Model Membranes," Biochem. Biophys. Acta., 1994, pp. 95-108, vol. 1197.

Wagner, R., "Gene Inhibition Using Antisense Oligodeoxynucleotides," Nature, 1994, pp. 333-335, vol. 372.

Wang et al., "Unmethylated CpG Motifs Protect Murine B Lymphocytes Against Fas-Mediated Apoptosis," Cellular Immunol., 1997, pp. 162-167, vol. 180.

Wyllie et al., "Cell Death: The Significance of Apoptosis," Int. Rev. Cytol., 1980, pp. 251-306, vol. 68.

Wyllie A., "Glucocorticoid-Induced Thymocyte Apoptosis is Associated with Endogenous Endonuclease Activation," Nature, 1980, pp. 555-556, vol. 284.

Yoong et al., "Fas/Fas Ligand Interaction in Human Colorectal Hepatic Metastases," Am. J. Pathol., Mar. 1999, pp. 693-703, vol. 154.

* cited by examiner

_US 7,157,436 B2_

SEQUENCE LISTING

```
<160> NUMBER OF SEQ ID NOS: 87

<210> SEQ ID NO 1
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 1
gtgtgtgtgt gtgtgtgtgt gtgtgtg                                   27

<210> SEQ ID NO 2
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 2
gggtgggtgg gtgggtgggt gggtggg                                   27
```

```
<210> SEQ ID NO 3
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 3
gggggtgggg gtgggggtgg gggtggg                                    27

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 4
gggggggtgg gggggtgggg gggtggg                                    27

<210> SEQ ID NO 5
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 5
tgtgtgtgtg tgtgtgtgtg tgtgtgt                                    27

<210> SEQ ID NO 6
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 6
tctctctctc tctctctctc tctctct                                    27

<210> SEQ ID NO 7
<211> LENGTH: 3
<212> TYPE: DNA
<213> ORGANISM: Artificial Sequence
<220> FEATURE:
<223> OTHER INFORMATION: Synthetic Oligonucleotide

<400> SEQUENCE: 7 tgt                                                               3

<210> SEQ ID NO 8
<211> LENGTH: 3
<212> TYPE: DNA
<213> ORGANISM: Artificial Sequence
<220> FEATURE:
<223> OTHER INFORMATION: Synthetic Oligonucleotide

<400> SEQUENCE: 8 gtg                                                               3

<210> SEQ ID NO 9
<211> LENGTH: 6
<212> TYPE: DNA
<213> ORGANISM: Artificial Sequence
<220> FEATURE:
<223> OTHER INFORMATION: Synthetic Oligonucleotide
```

```
<400> SEQUENCE: 9 tgtgtg                                                            6

<210> SEQ ID NO 10
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 10 gtgtgt                                                            6

<210> SEQ ID NO 11
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 11 tgtgtgtgt                                                         9

<210> SEQ ID NO 12
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 12 gtgtgtgtg                                                         9

<210> SEQ ID NO 13
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 13
tgtgtgtgtg tg                                                    12

<210> SEQ ID NO 14
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 14
gtgtgtgtgt gt                                                    12

<210> SEQ ID NO 15
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 15
tgtgtgtgtg tgtg                                                  14
```

```
<210> SEQ ID NO 16
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 16
gtgtgtgtgt gtgtg                                               15

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
tgtgtgtgtg tgtgtgtg                                            18

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18
gtgtgtgtgt gtgtgtgt                                            18

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
tgtgtgtgtg tgtgtgtgtg t                                        21

<210> SEQ ID NO 20
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 20
gtgtgtgtgt gtgtgtgtgt g                                        21

<210> SEQ ID NO 21
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 21
tgtgtgtgtg tgtgtgtgtg tgtg                                     24

<210> SEQ ID NO 22
<211> LENGTH: 24
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 22
gtgtgtgtgt gtgtgtgtgt gtgt                                    24

<210> SEQ ID NO 23
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 23 tttgtt                                                         6

<210> SEQ ID NO 24
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 24 ggtggg                                                         6

<210> SEQ ID NO 25
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 25 gggtgg                                                         6

<210> SEQ ID NO 26
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 26 ttgttt                                                         6

<210> SEQ ID NO 27
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 27 aagtaa                                                         6

<210> SEQ ID NO 28
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 28 ccgtcc                                                         6
```

```
<210> SEQ ID NO 29
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 29 tggttg                                                              6

<210> SEQ ID NO 30
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 30 atgtat                                                              6

<210> SEQ ID NO 31
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 31 aggtga                                                              6

<210> SEQ ID NO 32
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 32 gagtga                                                              6

<210> SEQ ID NO 33
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 33 gggtct                                                              6

<210> SEQ ID NO 34
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 34 ccgtgg                                                              6

<210> SEQ ID NO 35
<211> LENGTH: 6
<212> TYPE: DNA
<213> ORGANISM: Artificial Sequence
<220> FEATURE:
<223> OTHER INFORMATION: Synthetic Oligonucleotide
```

```
<400> SEQUENCE: 35 gggtcc                                                               6

<210> SEQ ID NO 36
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 36 ctgtct                                                               6

<210> SEQ ID NO 37
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 37 tcgttc                                                               6

<210> SEQ ID NO 38
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 38 cggtgc                                                               6

<210> SEQ ID NO 39
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 39 ttgtgg                                                               6

<210> SEQ ID NO 40
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 40 gggttt                                                               6

<210> SEQ ID NO 41
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 41 ggttgg                                                               6
```

-continued

```
<210> SEQ ID NO 42
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 42 ggaagg                                                                       6

<210> SEQ ID NO 43
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 43 ggccgg                                                                       6

<210> SEQ ID NO 44
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 44 gggggg                                                                       6

<210> SEQ ID NO 45
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 45 gggagg                                                                       6

<210> SEQ ID NO 46
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 46 gggcgg                                                                       6

<210> SEQ ID NO 47
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 47 ggaggg                                                                       6

<210> SEQ ID NO 48
<211> LENGTH: 6
<212> TYPE: DNA
<213> ORGANISM: Artificial Sequence
<220> FEATURE:
<223> OTHER INFORMATION: Synthetic Oligonucleotide
```

```
<400> SEQUENCE: 48 gtgggg                                                              6

<210> SEQ ID NO 49
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 49 ttaggg                                                              6

<210> SEQ ID NO 50
<211> LENGTH: 2
<212> TYPE: DNA
<213> ORGANISM: Artificial Sequence
<220> FEATURE:
<223> OTHER INFORMATION: Synthetic Oligonucleotide

<400> SEQUENCE: 50 gt                                                                  2

<210> SEQ ID NO 51
<211> LENGTH: 2
<212> TYPE: DNA
<213> ORGANISM: Artificial Sequence
<220> FEATURE:
<223> OTHER INFORMATION: Synthetic Oligonucleotide

<400> SEQUENCE: 51 tg                                                                  2

<210> SEQ ID NO 52
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 52 gtgg                                                                4

<210> SEQ ID NO 53
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 53 ttgt                                                                4

<210> SEQ ID NO 54
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 54 gtgt                                                                4
```

```
<210> SEQ ID NO 55
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 55 ttgg                                                                      4

<210> SEQ ID NO 56
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 56 ggtg                                                                      4

<210> SEQ ID NO 57
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 57 tgtt                                                                      4

<210> SEQ ID NO 58
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 58 ggtt                                                                      4

<210> SEQ ID NO 59
<211> LENGTH: 4
<212> TYPE: DNA
<213> ORGANISM: Artificial Sequence
<220> FEATURE:
<223> OTHER INFORMATION: Synthetic Oligonucleotide

<400> SEQUENCE: 59 tgtg                                                                      4

<210> SEQ ID NO 60
<211> LENGTH: 5
<212> TYPE: DNA
<213> ORGANISM: Artificial Sequence
<220> FEATURE:
<223> OTHER INFORMATION: Synthetic Oligonucleotide

<400> SEQUENCE: 60 ggtgg                                                                     5

<210> SEQ ID NO 61
<211> LENGTH: 5
<212> TYPE: DNA
<213> ORGANISM: Artificial Sequence
<220> FEATURE:
<223> OTHER INFORMATION: Synthetic Oligonucleotide
```

```
<400> SEQUENCE: 61 gggtg                                                            5

<210> SEQ ID NO 62
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 62 ggggtgg                                                          7

<210> SEQ ID NO 63
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 63 gggtggg                                                          7

<210> SEQ ID NO 64
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 64 tgggtgg                                                          7

<210> SEQ ID NO 65
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 65 gggtggt                                                          7

<210> SEQ ID NO 66
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 66
gtgtgtgtgt gtgtgtgtgt gtgtgtg                                   27

<210> SEQ ID NO 67
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 67
gggtgggtgg gtgggtgggt gggtggg                                   27
```

```
<210> SEQ ID NO 68
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 68
gggggtgggg gtgggggtgg gggtggg                                    27

<210> SEQ ID NO 69
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 69
gggggggtgg gggggtgggg gggtggg                                    27

<210> SEQ ID NO 70
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 70 tgtgtg                                                            6

<210> SEQ ID NO 71
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 71 gtgtgt                                                            6

<210> SEQ ID NO 72
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 72 tttgtt                                                            6

<210> SEQ ID NO 73
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 73 ggtggg                                                            6

<210> SEQ ID NO 74
<211> LENGTH: 6
<212> TYPE: DNA
<213> ORGANISM: Artificial Sequence
<220> FEATURE:
<223> OTHER INFORMATION: Synthetic Oligonucleotide
```

```
<400> SEQUENCE: 74 gggtgg                                                                    6

<210> SEQ ID NO 75
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 75 ttgttt                                                                    6

<210> SEQ ID NO 76
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 76
gccgagaagg tgcgcaacct gccggctggc cacggactga acgct             45

<210> SEQ ID NO 77
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 77
acgccgacgt cgtctgtggt ggggtgtcta ccgccaacgc gacgg             45

<210> SEQ ID NO 78
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 78
cgactacaac ggctgggata tcaacacccc ggcgttcgag tggta             45

<210> SEQ ID NO 79
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 79 ccaccc                                                                    6

<210> SEQ ID NO 80
<211> LENGTH: 5
<212> TYPE: DNA
<213> ORGANISM: Artificial Sequence
<220> FEATURE:
<223> OTHER INFORMATION: Synthetic Oligonucleotide

<400> SEQUENCE: 80 cggta                                                                     5
```

<210> SEQ ID NO 81
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 81
gtgtgtttgg t                                                          11

<210> SEQ ID NO 82
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 82
ggttttgttt g                                                          11

<210> SEQ ID NO 83
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 83
ttgttttttt tg                                                         12

<210> SEQ ID NO 84
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 84

Tyr Val Ala Asp
1

<210> SEQ ID NO 85
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 85

Asp Glu Val Asp
1

<210> SEQ ID NO 86
<211> LENGTH: 5
<212> TYPE: PRT
<213> ORGANISM: Artificial Sequence
<220> FEATURE:
<223> OTHER INFORMATION: Synthetic Peptide
<221> NAME/KEY: SITE
<222> LOCATION: (4)..(4)
<223> OTHER INFORMATION: X = Any Amino Acid

<400> SEQUENCE: 86

Ile Leu Glu Xaa Cys
1               5

```
<210> SEQ ID NO 87
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 87

Ile Glu Gly Asp
     1
```

THERAPEUTICALLY USEFUL SYNTHETIC OLIGONUCLEOTIDES

This patent application claims priority to U.S. provisional patent application Ser. No. 60/170,325, filed Dec. 13, 1999 and U.S. provisional patent application Ser. No. 60/228,925, filed Aug. 29, 2000.

FIELD OF THE INVENTION

The present invention relates to an oligonucleotide composition for the treatment of cancer.

BACKGROUND OF THE INVENTION

Cancer is an aberrant net accumulation of atypical cells, which can result from an excess of proliferation, an insufficiency of cell death, or a combination of the two.

Proliferation is the culmination of a cell's progression through the cell cycle resulting in the division of one cell into two cells. The 5 major phases of the cell cycle are $G_0$, $G_1$, S, $G_2$ and M. During the $G_0$ phase, cells are quiescent. Most cells in the body, at any one time, are in this stage. During the $G_1$ phase, cells, responding to signals to divide, produce the RNA and the proteins necessary for DNA synthesis. During the S-phase (SE, early S-phase; SM, middle S-phase; and SL, late S-phase) the cells replicate their DNA. During the $G_2$ phase, proteins are elaborated in preparation for cell division. During the mitotic (M) phase, the cell divides into two daughter cells. Alterations in cell cycle progression occur in all cancers and may result from over-expression of genes, mutation of regulatory genes, or abrogation of DNA damage checkpoints (Hochhauser D. Anti-Cancer Chemotherapeutic Agents 8:903, 1997).

Unlike cancer cells, most normal cells cannot proliferate indefinitely due to a process termed cellular senescence. Cellular senescence is a programmed cell death response leading to growth arrest of cells (Dimri et al. Proc. Natl. Acad. Sci. USA 92:20, 1995). DNA damage, exposure of colon, breast and ovarian cancer cells to toposiomerase inhibitors and exposure of nasopharyngeal cancer cells to cisplatin are reported to prevent proliferation of these cells by induction of senescence (Wang et al. Cancer Res. 58:5019, 1998; Poele et al. Br. J. Cancer 80:9, 1999).

Synthetic oligonucleotides are polyanionic sequences that are internalized in cells (Vlassov et al. Biochim. Biophys. Acta 1197:95, 1994). Synthetic oligonucleotides are reported that bind selectively to nucleic acids (Wagner, R. Nature: 372:333, 1994), to specific cellular proteins (Bates et al. J. Biol. Chem. 274:26369, 1999) and to specific nuclear proteins Scaggiante et al. Eur. J. Biochem. 252:207, 1998) to inhibit proliferation of cancer cells.

Synthetic 27 base sequences containing guanine (G) and variable amounts of thymine (T) (oligonucleotide GTn), wherein n is $\geq 1$ or $\leq 7$ and wherein the number of bases is $\geq 20$ (Scaggiante et al. Eur. J. Biochem. 252:207, 1998), are reported to inhibit growth of cancer cell lines by sequence specific binding to a 45 kDa nuclear protein, whereas GTn, wherein the number of bases is $\leq 20$, are reported to be inactive against cancer cell lines (Morassutti et al. Nucleosides and Nucleotides 18:1711, 1999). Two synthetic GT-rich oligonucleotides of 15 and 29 bases with 3' aminoalkyl modifications are reported to form G-quartets that bind to nucleolin and to inhibit proliferation of cancer cell lines (Bates et al. J. Biol. Chem. 274:26369, 1999). The synthetic 6 base TTAGGG-phosphorothioate, having a sequence identical to that of the mammalian telomere repeat sequence, is reported to inhibit proliferation of Burkitt's lymphoma cells in vitro and in vivo (Mata et al. Toxicol. Applied Pharmacol. 144:189, 1997). However, the synthetic 6 base TTAGGG-phosphodiester is reported to have no anti-telomerase activity (U.S. Pat. No: 5,643,890).

Cell death is effected by immune-mediators that promote apoptosis, and by apoptosis inducers that directly initiate pathways leading to cell death (Muzio et al. Cell 85:817, 1996; Levine, A. Cell 88:323, 1997). Apoptosis is an active cellular death process characterized by distinctive morphological changes that include condensation of nuclear chromatin, cell shrinkage, nuclear disintegration, plasma membrane blebbing, and the formation of membrane-bound apoptotic bodies (Wyllie et al. Int. Rev. Cytol. 68:251, 1980). A molecular hallmark of apoptosis is degradation of the cell's nuclear DNA into oligonucleosomal-length fragments as the result of activation of endogenous endonucleases (Wyllie A. Nature 284:555, 1980).

Caspases (cysteine-aspartyl-specific proteases) have been implicated as key enzymes in the execution of the late stage of apoptosis. The caspase family consists of at least fourteen related cysteine aspartyl proteases. All the caspases contain a conserved QACXG (where X is R, Q or G) pentapeptide activesite motif (Cohen G. Biochim. Biophys. Acta 1366: 139, 1997). A number of caspases are synthesized as inactive proenzymes that are activated following cleavage at caspase specific cleavage sites (Cohen G. Biochim. Biophys. Acta 1366:139, 1997) or as inactive enzymes that require association with regulatory molecules for activation (Stennicke et al. J. Biol. Chem. 274:8359, 1999).

In addition to their role in apoptosis, caspases are involved in activation and proliferation of B and T lymphocytes, in cytokine maturation during inflammation, in differentiation of progenitor cells during erythropoiesis and in development of lens fiber (Fadeel et al. Leukemia 14:1514, 2000). With respect to B and T lymphocytes, caspase 3 is processed during activation of B lymphocytes and of CD4 (+), CD8 (+), CD45RA(+) and CD45RO (+) subsets of T lymphocytes (Alam et al. J. Exp. Med. 190:1879, 1999). Moreover, stimulation of T lymphocytes by mitogens and by interleukin-2 is associated with activation of the caspase pathway and with cleavage of PARP (Wilheim et al. Eur. J. Immunol. 28:891, 1998). With respect to cytokines, caspase 3 activity is necessary for the release of IL-2 by activated T lymphocytes (Posmantur et al. Exp. Cell Res. 244:302, 1998) and for the processing and maturation of the pro-inflammatory cytokine interleukin-16 (Zhang et al. J. Biol. Chem. 273:1144, 1998). With respect to erythropoiesis, caspase activation is involved in erythropoiesis regulation and has been shown to modulate GATA-1, a nuclear regulatory protein crucial for the maturation of erythroid precursors (De Maria, et al. Nature 401:489, 1999).

Cytolysis is the complete or partial destruction of a cell and is mediated by the immune system. Activated macrophages and monocytes produce bioactive molecules that include, but are not limited to cytokines. Cytokines, include, but are not limited to, interleukin (IL)-1, IL-1 beta, IL-6, IL-10, IL-12, and TNF-alpha.

IL-1 beta reduces bone marrow cell sensitivity to cytoreductive drugs, to radiation and to in vitro tumor cell purging with drugs in autologous bone marrow transplantation (Dalmau et al. Bone Marrow Transplant. 12:551, 1993).

IL-6 induces B cell differentiation, stimulates IgG secretion (Taga et al. J. Exp. Med. 166:967, 1987), induces cytotoxic T cell differentiation (Lee et al. Vaccine 17:490, 1999), promotes megakaryocyte maturation (Ishibashi et al. Proc. Natl. Acad. Sci. USA 86:8953, 1989) and functions both as an anti-proliferative factor (Mori et al. Biochem. Biophys. Res. Comm. 257:609, 1999; Alexandroff et al. Biochem. Soc. Trans. 25:270, 1997; Takizawa et al. Cancer Res. 53:18, 1993: Novick et al. Cytokine 4:6, 1992) and as a pro-proliferative factor (Okamoto et al. Cancer Res. 57:141, 1997; Okamoto et al. Int. J. Cancer 72:149, 1997; Chiu et al. Clin. Cancer Res. 2:215, 1996; Lu et al. Clin. Cancer Res. 2:1417, 1996) for cancer cells.

IL-10 enhances the effectiveness of vaccines in murine tumor models (Kauffman et al. J. Immunother. 22: 489, 1999) and up-regulates anti-cancer autoreactive T cell responses (Alleva et al. Immunobiol. 192:155, 1995).

IL-12, alone and in combination with other cytokines, promotes the maturation of leukocytes and induces the secretion of interferon-gamma. IL-12 is reported to have anti-cancer activity (Stine et al. Annals NY Academy of Science 795:420, 1996; Chen et al. Journal of Immunol. 159:351, 1997) including, but not limited to, activation of specific cytolytic T-lymphocytes, activation of natural killer (NK) cells and induction of the anti-angiogenic proteins IP-10 and MiG.

TNF-alpha causes necrosis of solid tumors (Porter et al. Trends in Biotech. 9:158, 1991), sensitizes cancer cells to gamma irradiation-induced apoptosis (Kimura et al. Cancer Res. 59:1606, 1999) and protects bone marrow precursor cells from the effects of antineoplastic agents (Dalmau et al. Bone Marrow Transplant. 12:551, 1993).

However, most prior art anti-cancer therapies, whether directed to induction of cell cycle arrest, inhibition of proliferation, induction of apoptosis or stimulation of the immune system, have proven to be less than adequate for clinical applications. Many of these therapies are inefficient or toxic, have significant adverse side effects, result in development of drug resistance or immunosensitization, and are debilitating for the recipient Therefore, there is a continuing need for novel compositions and methods that induce cell cycle arrest in cancer cells, inhibit proliferation of cancer cells, activate caspases in cancer cells, induce apoptosis in cancer cells and stimulate cytokine production by immune system cells.

SUMMARY OF THE INVENTION

The present invention fulfills this need by providing a composition and method comprising a 2 to 20 base 3'-OH, 5'-OH synthetic oligonucleotide (hereinafter "sequence") selected from the group consisting of $(G_xT_y)_n$, $(T_yG_x)_n$, $a(G_xT_y)_n$, $a(T_yG_x)_n$, $(G_xT_y)_nb$, $a(T_yG_x)_nb$, $a(G_xT_y)_nb$, $a(T_yG_x)_nb$, wherein x and y is an integer between 1 and 7, n is an integer between 1 and 12, a and b are one or more As, Cs, Gs or Ts, and wherein the sequence induces a response selected from the group consisting of induction of cell cycle arrest, inhibition of proliferation, activation of caspases and induction of apoptosis in cancer cells and production of cytokines by immune system cells.

A composition comprising a sequence and a pharmaceutically acceptable carrier is administered to an animal, including a human, having cancer in an amount effective to treat the cancer in the animal. The unexpected and surprising ability of the sequence to induce cell cycle arrest, inhibit proliferation, activate caspases and induce apoptosis and in cancer cells and to stimulate cyotkine production by immune system cells addresses a long felt unfulfilled need in the medical arts and provides an important benefit for animals, including humans.

Accordingly, it is an object of the present invention is to provide a composition and method effective to treat a disease in an animal, including a human.

Another object of the present invention is to provide a composition and method effective to treat a cancer.

Another object of the present invention is to provide a composition and method that induces senescence in cells.

Another object of the present invention is to provide a composition and method that induces cell cycle arrest in cells.

Another object of the present invention is to provide a composition and method that induces cell cycle arrest in cancer cells.

Another object of the present invention is to provide a composition and method that inhibits proliferation of cells.

Another object of the present invention is to provide a composition and method that inhibits proliferation of cancer cells.

Another object of the present invention is to provide a composition and method that induces apoptosis in cells.

Another object of the present invention is to provide a composition and method that induces apoptosis in cancer cells.

Another object of the present invention is to provide a composition and method that induces apoptosis in cancer cells independent of Fas.

Another object of the present invention is to provide a composition and method that induces apoptosis in cancer cells independent of TNFR1.

Another object of the present invention is to provide a composition and method that induces apoptosis in cancer cells independent of p53/p21.

Another object of the present invention is to provide a composition and method that induces apoptosis in cancer cells independent of p21/waf-1/CIP.

Another object of the present invention is to provide a composition and method that induces apoptosis in cancer cells independent of $p15^{ink4B}$.

Another object of the present invention is to provide a composition and method that induces apoptosis in cancer cells independent of $p16^{ink4}$.

Another object of the present invention is to provide a composition and method that induces apoptosis in cancer cells independent of caspase 3.

Another object of the present invention is to provide a composition and it method that induces apoptosis in cancer cells independent of TGF-beta 1 receptor.

Another object of the present invention is to provide a composition and method that induces apoptosis in cancer cells independent of hormone dependence.

Another object of the present invention is to provide a composition and method that induces apoptosis in cancer cells independent of drug resistance.

Another object of the present invention is to provide a composition and method that activates caspases in cells.

Another object of the present invention is to provide a composition and method that activates caspases in cancer cells.

Another object of the present invention is to provide a composition and method to treat an autoimmune disease.

Another object of the present invention is to provide a composition and method to treat a lymphoproliferative disease.

Another object of the present invention is to provide a composition and method to treat an infection.

Another object of the present invention is to provide a composition and method to treat an inflammation.

Another object of the present invention is to provide a composition and method to modulate T- or B-cell activation.

Another object of the present invention is to provide a composition and method to modulate progenitor cell maturation.

Another object of the present invention is to provide a composition and method to modulate erythropoiesis.

Another object of the present invention is to provide a composition and method to modulate transcription factors in cells.

Another object of the present invention is to provide a composition and method that potentiates the effect of other therapeutic agents on cells.

Another object of the present invention is to provide a composition and method that potentiates the effect of chemotherapeutic agents on cancer cells.

Another object of the present invention is to provide a composition and method that potentiates the anti-neoplastic effect of radiation.

Another object of the present invention is to provide a composition and method that stimulates cytokine production by cells of the immune system.

Another object of the present invention is to provide a composition and method that stimulates IL-1 beta production by cells of the immune system.

Another object of the present invention is to provide a composition and method that stimulates IL-6 production by cells of the immune system.

Another object of the present invention is to provide a composition and method that stimulates IL-10 production by cells of the immune system.

Another object of the present invention is to provide a composition and method that stimulates IL-12 production by cells of the immune system.

Another object of the present invention is to provide a composition and method that stimulates TNF-$_\alpha$ production by cells of the immune system.

Another object of the present invention is to provide a composition that is simple to prepare.

Another object of the present invention is to provide a composition that is minimally toxic to the recipient.

These and other objects, features and advantages of the present invention will become apparent after a review of the following detailed description of the disclosed embodiment and the appended claims.

DETAILED DESCRIPTION OF THE INVENTION

Figure 1:
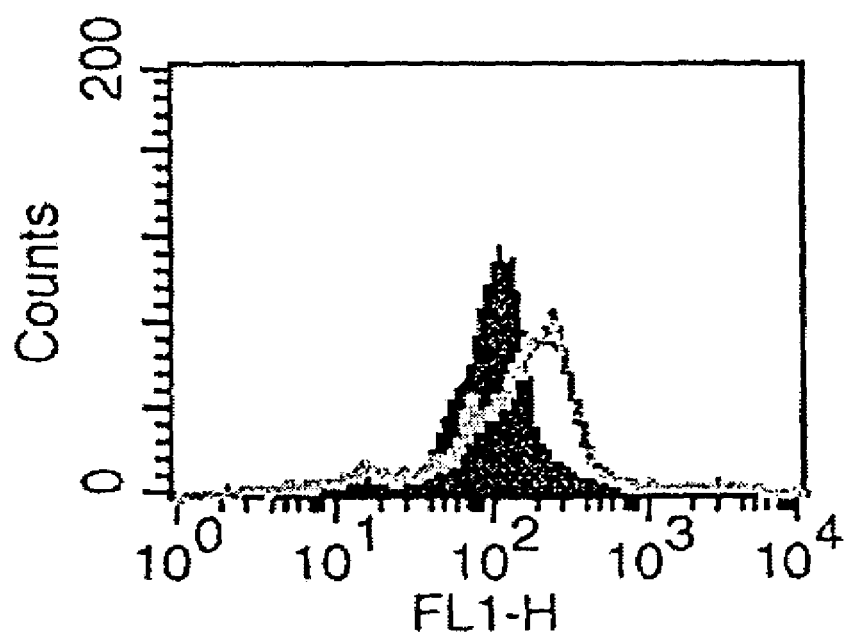
FIG. 1. Fluorescence [Fluo-3-AM] of Jurkat human T leukemia cells incubated with 0 µg/ml and 100 µg/ml of 6 base GT SEQ ID NO:25.

The present invention provides a composition comprising a 2 to 20 base 3'-OH, 5'-OH synthetic oligonucleotide (sequence) selected from the group consisting of $(G_xT_y)_n$, $(T_yG_x)_n$, $a(G_xT_y)_n$, $a(T_yG_y)_n$, $(G_xT_y)_nb$, $(T_yG_x)_nb$, $a(G_xT_y)_nb$, $a(T_yG_x)_nb$, wherein x and y is an integer between 1 and 7, n is an integer between 1 and 12, a and b are one or more As, Cs, Gs or Ts, wherein the sequence induces a response selected from the group consisting of induction of cell cycle arrest, inhibition of proliferation, activation of caspases and induction of apoptosis in cancer cells and production of cytokines by immune system cells.

A composition comprising a sequence and a pharmaceutically acceptable carrier is administered to an animal, including a human, having cancer in an amount effective to treat the cancer in the animal, including the human. The unexpected and surprising ability of the sequence to induce cell cycle arrest, inhibit proliferation, induce apoptosis and activate caspases in cancer cells and to stimulate cytokine production by immune system cells addresses a long felt unfulfilled need in the medical arts and provides an important benefit for animals, including humans.

As used herein the word "sequence" refers to a 2 to 20 base 3'-OH, 5'-OH synthetic oligonucleotide comprising A, C, G and T bases.

As used herein, the abbreviations "GT", "AG", "CG", "GG", "AGT" and "CGT" refer to sequences comprising the named bases synthesized in any order.

As used herein, the word "response" refers to induction of cell cycle arrest, inhibition of proliferation, activation of caspases and induction of apoptosis, in cancer cells and stimulation of cytokine production by immune system cells.

As used herein, the phrases "therapeutic treatment" and "amount effective to" refer to an amount of a sequence effective to induce cell cycle arrest, inhibit proliferation, activate caspases and induce apoptosis in cancer cells and stimulate cytokine production by immune system cells.

As used herein, the phrases "suspension tumor model" and "solid tumor models" refer to primary or secondary carcinomas or sarcomas".

As used herein, the phrase "chemotherapeutic" is any agent approved by a regulatory agency of a country or a state government or listed in the U.S. Pharmacopoeia or other generally recognized pharmacopoeia to treat cancer in an animal, including a human.

As used herein, the word "antineoplastic" refers to preventing the development, maturation, proliferation or spread of cancer cells.

As used herein, the word "potentiates" refers to a degree of synergism that is greater than the additive activity of each agent.

As used herein, the word "synergism" refers to the coordinated action of two or more agents.

Administration of an effective amount of a sequence of the present invention to an animal, including a human, is a therapeutic treatment that prevents, treats or eliminates a disease including, but not limited to, cancer, rheumatoid arthritis, lympho-proliferative disorders and asthma. Cancers include, but are not limited to, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma and metastases derived therefrom.

The therapeutic effectiveness of a sequence may be increased by methods including, but not limited to, chemically modifying the base, sugar or phosphate backbone, chemically supplementing or biotechnologically amplifying the sequences using bacterial plasmids containing the appropriate sequences, complexing the sequences to biological or chemical carriers or coupling the sequences to tissue-type or cell-type directed ligands or antibodies Compositions comprising one or more sequences and a pharmaceutically acceptable carrier are prepared by uniformly and intimately bringing into association the sequence and the pharmaceutically acceptable carrier. Pharmaceutically acceptable carriers include liquid carriers, solid carriers or both. Liquid carriers are aqueous carriers, non-aqueous carriers or both and include, but are not limited to, aqueous suspensions, oil emulsions, water in oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, viral vector systems, particles, microparticles, nanoparticles, microspheres, nanospheres, minipumps, bacterial cell wall extracts and biodegradable or non-biodegradable natural or synthetic polymers that allow for sustained release of the sequences. Methods used to complex a sequence to a solid carrier include, but are not limited to, direct adsorption to the surface of the solid carrier; covalent coupling to the surface of the solid carrier, either directly or via a linking moiety; and covalent coupling to the polymer used to make the solid carrier. Optionally, a sequence can be stabilized by the addition of non-ionic or ionic polymers such as polyoxyethylenesorbitan monooleates (Tweens) or hyaluronic acid.

Preferred aqueous carriers include, but are not limited to, water, saline and pharmaceutically acceptable buffers. Preferred non-aqueous carriers include, but are not limited to, a mineral oil and a neutral oil and mixtures thereof. Optionally, excipients may be included regardless of the pharmaceutically acceptable carrier used to present the sequence to the responding cells. These excipients include, but are not limited to, anti-oxidants, buffers, and bacteriostats, and may include suspending agents and thickening agents.

One or more sequences may be administered alone, or in combination with other therapeutic modalities including, but not limited to, chemotherapeutic agents, immunotherapeutic agents, antimicrobial agents, antiviral agents or in combination with radiation therapy. Chemotherapeutic agents include, but are not limited to, anti-metabolites, DNA damaging, microtubule destabilizing, microtubule stabilizing, actin depolymerizing, growth inhibiting, topoisomerase inhibiting, HMG-CoA inhibiting, purine inhibiting, pyrimidine inhibiting, metaloproteinase inhibiting, CDK inhibiting, angiogenesis inhibiting and differentiation enhancing agents.

Routes of administration include, but are not limited to, oral, topical, subcutaneous, transdermal, subdermal, intramuscular, intra-peritoneal, intra-vesical, intra-articular, intra-arterial, intra-venous, intra-dermal, intra-cranial, intra-lesional, intra-tumoral, intra-ocular, intra-pulmonary, intra-spinal, intra-prostatic, placement within cavities of the body, nasal inhalation, pulmonary inhalation, impression into skin and electrocorporation.

Depending on the route of administration, the volume per dose is preferably about 0.001 to 100 ml per dose, more preferably about 0.01 to 50 ml per dose and most preferably about 0.1 to 30 ml per dose. Preferably, the amount of sequence administered per dose is from about 0.001 to 100 mg/kg, more preferably from about 0.01 to 10 mg/kg and most preferably from about 0.1 to 5 mg/kg. The sequence or sequence plus a therapeutic agent can be administered in a single dose treatment, in multiple dose treatments or continuously infused on a a schedule and over a period of time appropriate to the disease being treated, the condition of the recipient and the route of administration. Moreover, the sequence can be administered before, at the same time as, or after administration of the therapeutic agent.

A sequence in combination with chemotherapeutic agent is administered to an animal having cancer in an amount effective to potentiate the anti-neoplastic effect of the chemotherapeutic agent. Preferably, the amount of therapeutic agent administered per dose is from about 0.001 to 1000 mg/m$^2$ or from about 0.01 to 1000 mg/kg, more preferably from about 0.01 to 500 mg/m$^2$ or from about 0.01 to 500 mg/kg and most preferably from about 0.1 to 100 mg/m$^2$ or from about 0.1 to 100 mg/kg. The particular sequence and the particular therapeutic agent administered, the amount per dose, the dose schedule and the route of administration should be decided by the practitioner using methods known to those skilled in the art and will depend on the type of cancer, the severity of the cancer, the location of the cancer and other clinical factors such as the size, weight and physical condition of the recipient. In addition, in vitro assays may optionally be employed to help identify optimal ranges for sequence administration and for sequence plus therapeutic agent administration.

Although not wanting to be bound by the following hypothesis, it is thought that the sequences of the present invention form a new family of structures and that they do not function as antisense RNAs, antisense DNAs, triple helix forming DNAs, telomerase inhibitors, transcription activators or transcription inhibitors.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the invention.

EXAMPLE 1

Preparation of Sequences

Phosphodiester and phosphorothioate sequences were prepared by HUKABEL Scientific Ltd, (Montréal, Québec, Canada) using the EXPEDITE™ 8900 automated DNA synthesis system (PersSeptive Biosystems, Inc., Farmingham, Mass.) and by Sigma-Genosys (Woodlands, Tex.) using Abacus Segmented Synthesis Technology. Unless stated otherwise, the sequences used were phosphodiester sequences. Unless stated otherwise, immediately prior to use, the sequences were dispersed in autoclaved deionized water or in an autoclaved pharmaceutically acceptable buffer such as, but not limited to, saline.

EXAMPLE 2

Cells and Reagents

All cell lines were obtained from the American Type Culture Collection (ATCC, Rockville, Md.) and were cultured in the medium recommended by the ATCC. Table 1 shows the cell lines, their origins and their properties.

TABLE 1

Cell lines

| CELL LINE | ORIGIN | PROPERTIES |
|---|---|---|
| THP-1 | Human acute monocytic leukemia | Suspension tumor model<br>p53 null |
| MCF-7 | Human breast cancer | Solid tumor model; non-metastatic<br>Caspase 3-negative; estrogen-dependent |
| JURKAT | Human T cell leukemia | Suspension tumor model<br>Atypical multi-drug resistance<br>associated with p190-MRP protein |
| PC-3 | Human prostate cancer | Solid tumor model; metastatic<br>p53 mutated; androgen-independent<br>(hormone refractory) |
| LNCaP | Human prostate cancer | Solid tumor model; metastatic<br>TGF-beta 1 receptor-negative;<br>androgen-dependent |
| OVCAR-3 | Human ovarian cancer | Solid tumor model; metastatic<br>p53 mutated; p21/waf-1/Cip-1 deleted |
| SK-OV-3 | Human ovarian cancer | Solid tumor model; metastatic<br>p53 deleted; p21/waf-1/Cip deleted;<br>p15$^{snk4B}$, p16$^{ink4}$ deleted |
| HL-60 | Human promyelocytic leukemia | Suspension tumor model<br>p53 mutated |
| EL-4 | Murine T lymphoma | Suspension tumor model |
| A20 | Murine B cell leukemia | Suspension tumor model |
| L-1210 | Murine leukemia | Suspension tumor model |
| D-17 | Canine osteosarcoma | Solid tumor model |
| CF-51 | Canine mammary gland cancer | Solid tumor model |

Cells were seeded in 6 (1 ml/well), 24 (0.5 ml/well) or 96 (0.1 ml/well) well flat-bottom microplates and were maintained at 37° C. in a 5% $CO_2$ atmosphere. Unless stated otherwise, $2.5 \times 10^5$ cells/ml were incubated with 0 μg/ml (control) and 100 μg/ml (treated) of 2 to 45 base sequences containing A, C, G and T for 48 h.

EXAMPLE 3

Measurement of Cell Proliferation

Cell proliferation was measured using dimethylthiazol-diphenyl-tetrazolium (MTT) reduction (Mosman et al. J. Immunol. Methods 65:55, 1983). MTT was measured at a wavelength of 570 nm using a multiplate spectrophotometer reader (ELX800, Bio-TEK Instruments Inc., Winooski, Vt.).

EXAMPLE 4

Inhibition of Jurkat Human Leukemia T Cell Proliferation

Jurkat human leukemia T cells are an atypical multi-drug resistant human suspension tumor cell model. Jurkat cells were incubated with 27 base GT and CT sequences (Table 2).

TABLE 2

% inhibition of Jurkat human leukemia T cell proliferation

| SEQUENCE | % INHIBITION |
|---|---|
| GTGTGTGTGTGTGTGTGTGTGTGTGTG-(GT)$_{13}$G<br>SEQ ID NO:1-(27 bases) | 51 |
| GGGTGGGTGGGTGGGTGGGTGGGTGGG-(G$_3$T)$_6$G$_3$<br>SEQ ID NO:2-(27 bases) | 23 |
| GGGGGTGGGGGTGGGGGTGGGGGTGGG-(G$_5$T)$_4$G$_3$<br>SEQ ID NO:3-(27 bases) | 24 |
| GGGGGGGTGGGGGGGTGGGGGGGTGG-(G$_7$T)$_3$G$_3$<br>SEQ ID NO:4-(27 bases) | 11 |
| TGTGTGTGTGTGTGTGTGTGTGTGTG-(TG)$_{13}$T)<br>SEQ ID NO:5-(27 bases) | 45 |
| TCTCTCTCTCTCTCTCTCTCTCTCTCT-(TC)$_{13}$T<br>SEQ ID NO:6-(27 bases) | 0 |

As shown in Table 2, Jurkat T cell proliferation was inhibited by the GT sequences tested, but not by the CT sequence tested.

Jurkat T cells were incubated with 3, 6, 9, 12, 14, 15, 18, 21 and 24 base GT sequences (Table 3).

TABLE 3

% inhibition of Jurkat human leukemia T cell proliferation

| SEQUENCE | % INHIBITION |
|---|---|
| TGT-(TG)$_1$T<br>SEQ ID NO:7-(3 bases) | 22 |
| GTG-(GT)$_1$G<br>SEQ ID NO:8-(3 bases) | 46 |
| TGTGTG-(TG)$_3$<br>SEQ ID NO:9-(6 bases) | 36 |
| GTGTGT-(GT)$_3$<br>SEQ ID NO:10-(6 bases) | 48 |
| TGTGTGTGT-(TG)$_4$T<br>SEQ ID NO:11-(9 bases) | 45 |
| GTGTGTGTG-(GT)$_4$G<br>SEQ ID NO:12-(9 bases) | 47 |
| TGTGTGTGTGTG-(TG)$_6$<br>SEQ ID NO:13-(12 bases) | 49 |
| GTGTGTGTGTGT-(GT)$_6$<br>SEQ ID NO:14-(12 bases) | 51 |
| TGTGTGTGTGTGTG-(TG)$_7$<br>SEQ ID NO:15-(14 bases) | 47 |

TABLE 3-continued

% inhibition of Jurkat human leukemia T cell proliferation

| SEQUENCE | % INHIBITION |
|---|---|
| GTGTGTGTGTGTGTG-(GT)$_7$G | 58 |
| SEQ ID NO:16-(15 bases) | |
| TGTGTGTGTGTGTGTGTG-(TG)$_9$ | 56 |
| SEQ ID NO:17-(18 bases) | |
| GTGTGTGTGTGTGTGTGT-(GT)$_9$ | 60 |
| SEQ ID NO:18-(18 bases) | |
| TGTGTGTGTGTGTGTGTGTGT-(TG)$_{10}$T | 60 |
| SEQ ID NO:19-(21 bases) | |
| GTGTGTGTGTGTGTGTGTGTG-(GT)$_{10}$G | 46 |
| SEQ ID NO:20-(21 bases) | |
| TGTGTGTGTGTGTGTGTGTGTGTG-(TG)$_{12}$ | 54 |
| SEQ ID NO:21-(24 bases) | |
| GTGTGTGTGTGTGTGTGTGTGTGT-(GT)$_{12}$ | 56 |
| SEQ ID NO:22-(24 bases) | |

As shown in Table 3, 3, 6, 9, 12, 14, 15 and 18 base GT sequences inhibited Jurkat T cell proliferation as effectively as 21 and 24 bases GT sequences.

Jurkat T cells were incubated with 6 base GT, AG, CG, GG, AGT and CGT sequences (Table 4).

TABLE 4

% inhibition Jurkat human leukemia T cell proliferation

| SEQUENCE | % INHIBITION |
|---|---|
| TGTGTG-(TG)$_3$ | 36 |
| SEQ ID NO:9-(6 bases) | |
| GTGTGT-(GT)$_3$ | 48 |
| SEQ ID NO:10-(6 bases) | |
| TTTGTT-TT(TG)$_1$TT | 31 |
| SEQ ID NO:23-(6 bases) | |
| GGTGGG-GG(TG)$_1$GG | 48 |
| SEQ ID NO:24-(6 bases) | |
| GGGTGG-GG(GT)$_1$GG | 60 |
| SEQ ID NO:25-(6 bases) | |
| TTGTTT-TT(GT)$_1$TT | 34 |
| SEQ ID NO:26-(6 bases) | |
| AAGTAA-AA(GT)$_1$AA | 13 |
| SEQ ID NO:27-(6 bases) | |
| CCGTCC-CC(GT)$_1$CC | 11 |
| SEQ ID NO:28-(6 bases) | |
| TGGTTG-TG(GT)$_1$TG | 42 |
| SEQ ID NO:29-(6 bases) | |
| ATGTAT-AT(GT)$_1$AT | 16 |
| SEQ ID NO:30-(6 bases) | |
| AGGTGA-AG(GT)$_1$GA | 10 |
| SEQ ID NO:31-(6 bases) | |
| GAGTGA-GA(GT)$_1$GA | 24 |
| SEQ ID NO:32-(6 bases) | |
| GGGTCT-GG(GT)$_1$CT | 15 |
| SEQ ID NO:33-(6-bases) | |
| CCGTGG-CC(GT)$_1$GG | 37 |
| SEQ ID NO:34-(6 bases) | |
| GGGTCC-GG(GT)$_1$CC | 20 |
| SEQ ID NO:35-(6 bases) | |
| CTGTCT-CT(GT)$_1$CT | 19 |
| SEQ ID NO:36-(6 bases) | |
| TCGTTC-TC(GT)$_1$TC | 20 |
| SEQ ID NO:37-(6 bases) | |
| CGGTGC-CG(GT)$_1$GC | 16 |
| SEQ ID NO:38-(6 bases) | |
| TTGTGG-TT(GT)$_1$GG | 35 |
| SEQ ID NO:39-(6 bases) | |
| GGGTTT-GG(GT)$_1$TT | 31 |
| SEQ ID NO:40-(6 bases) | |
| GGTTGG-GG(TT)$_1$GG | 43 |
| SEQ ID NO:41-(6 bases) | |
| GGAAGG-GG(AA)$_1$GG | 22 |
| SEQ ID NO:42-(6 bases) | |

TABLE 4-continued

% inhibition Jurkat human leukemia T cell proliferation

| SEQUENCE | % INHIBITION |
|---|---|
| GGCCGG-GG(CC)GG | 29 |
| SEQ ID NO:43-(6 bases) | |
| GGGGGG-GG(GG)$_1$GG | 26 |
| SEQ ID NO:44-(6 bases) | |
| GGGAGG-GG(GA)$_1$GG | 28 |
| SEQ ID NO:45-(6 bases) | |
| GGGCGG-GG(GC)$_1$GG | 23 |
| SEQ ID NO:46-(6 bases) | |
| GGAGGG-GG(AG)$_1$GG | 14 |
| SEQ ID NO:47-(6 bases) | |
| GTGGGG-(GT)$_1$G$_4$ | 26 |
| SEQ ID NO:48-(6 bases) | |
| TTAGGG-TT(AG)$_1$GG | 45 |
| SEQ ID NO:49-(6 bases) | |

As shown in Table 4, 6 base GT sequences inhibited Jurkat T cell proliferation. GT SEQ ID NO:25 inhibited proliferation 60% and AGT SEQ ID NO:49 inhibited proliferation 45%. Comparison of the relative potency of GT SEQ ID NO:25 and AGT SEQ ID NO:49 using PHARM/PCS-4 Software (Microcomputer Specialists, Philadelphia, Pa.) showed the potency of GT SEQ ID NO:25 to be 3.4 times that of AGT SEQ ID NO:49. AGT SEQ ID NO:49-phosphorothioate is reported to inhibit telomerase activity and to induce apoptosis in Burkitt lymphoma cells (Mata et al. Toxicol. Appl. Pharmacol. 144:189, 1997).

To determine telomerase activity, extracts from $2 \times 10^5$ Jurkat T cells were assayed using the PCR-telomeric repeat amplification protocol (TRAP) (Roche, Laval, Québec, Canada). At concentrations between 1 and 100 µg/ml, GT SEQ ID NO:25-phosphodiester showed between 0 and 10% anti-telomerase activity, whereas AGT SEQ ID NO:49-phosphorothioate showed between 30 and 75% anti-telomerase activity. Neither GT SEQ ID NO:25-phosphorothioate nor GT SEQ ID NO:49-phosphodiester showed any anti-telomerase actvity.

Jurkat T cells were incubated with 2, 3, 4, 5, 6 and 7 base GT sequences (Table 5).

TABLE 5

% inhibition of Jurkat human leukemia T cell proliferation

| SEQUENCE | % INHIBITION |
|---|---|
| GT-(GT)$_1$ | 38 |
| SEQ ID NO:50-(2 bases) | |
| TG-(TG)$_1$ | 50 |
| SEQ ID NO:51-(2 bases) | |
| TGT-(TG)$_1$T | 22 |
| SEQ ID NO:7 (3 bases) | |
| GTG-(GT)$_1$6 | 46 |
| SEQ ID NO:8-(3 bases) | |
| GTGG-G(TG)$_1$G | 52 |
| SEQ ID NO:52-(4 bases) | |
| TTGT-T(GT)$_1$T | 25 |
| SEQ ID NO:53-(4 bases) | |
| GTGT-G(TG)$_1$T | 42 |
| SEQ ID NO:54-(4 bases) | |
| TTGG-T(TG)$_1$G | 44 |
| SEQ ID NO:55-(4 bases) | |
| GGTG-G(GT)$_1$G | 54 |
| SEQ ID NO:56-(4 bases) | |
| TGTT-T(GT)$_1$T | 32 |
| SEQ ID NO:57-(4 bases) | |
| GGTT-G(GT)$_1$T | 37 |
| SEQ ID NO:58-(4 bases) | |
| TGTG-T(GT)$_1$G | 52 |
| SEQ ID NO:59-(4 bases) | |

TABLE 5-continued

% inhibition of Jurkat human leukemia T cell proliferation

| SEQUENCE | % INHIBITION |
|---|---|
| GGTGG-G(GT)$_1$G$_2$ SEQ ID NO:60-(5 bases) | 50 |
| GGGTG-G2(GT)G SEQ ID NO:61-(5 bases) | 50 |
| TGTGTG-(TG)$_3$ SEQ ID NO:9-(6 bases) | 36 |
| GTGTGT-(GT)$_3$ SEQ ID NO:10-(6 bases) | 48 |
| TTTGTT-TT(TG)$_1$TT SEQ ID NO:23-(6 bases) | 31 |
| GGTGGG-GG(GT)$_1$GG SEQ ID NO:24-(6 bases) | 48 |
| GGGTGG-GG(GT)$_1$GG SEQ ID NO:25-(6 bases) | 60 |
| TTGTTT-TT(GT)$_1$TT SEQ ID NO:26-(6 bases) | 34 |
| TGGTTG-TG(GT)$_1$TG SEQ ID NO:29-(6 bases) | 42 |
| GGGGTGG-G$_3$(GT)$_1$G$_2$ SEQ ID NO:62-(7 bases) | 41 |
| GGGTGGG-G$_2$(GT)G$_3$ SEQ ID NO:63-(7 bases) | 28 |
| TGGGTGG-TG$_2$(GT)$_1$G$_2$ SEQ ID NO:64-(7 bases) | 55 |
| GGGTGGT-G$_2$(GT)$_1$G$_2$T SEQ ID NO:65-(7 bases) | 48 |

As shown in Table 5, 2, 3, 4, 5, 6 and 7 base GT sequences inhibited Jurkat T cell proliferation.

EXAMPLE 5

Inhibition of HL-60 Human Promyelocytic Leukemia Cell Proliferation

HL-60 promyelocytic leukemia cells are a p53 mutated human suspension tumor model. HL-60 cells were incubated with 6 base GT sequences (Table 6).

TABLE 6

% inhibition of HL-60 human promyelocytic leukemia cell proliferation

| SEQUENCE | % INHIBITION |
|---|---|
| TGTGTG-(TG)$_3$ SEQ ID NO:9-(6 bases) | 7 |
| GTGTGT-(GT)$_3$ SEQ ID NO:10-(6 bases) | 13 |
| TTTGTT-TT(TG)$_1$TT SEQ ID NO:23-(6 bases) | 13 |
| GGTGGG-GG(TG)$_1$GG SEQ ID NO:24-(6 bases) | 18 |
| GGGTGG-GG(GT)$_1$GG SEQ ID NO:25-(6 bases) | 35 |
| TTGTTT-TT(GT)$_1$TT SEQ ID NO:26-(6 bases) | 16 |

As shown in Table 6, 6 base GT sequences inhibited HL-60 cell proliferation.

EXAMPLE 6

Inhibition of MCF-7 Human Breast Cancer Cell Proliferation

MCF-7 human breast cancer cells are a caspase 3 negative, estrogen-dependent human solid tumor model. MCF-7 cells ($5\times10^5$ cells/ml) were incubated with 3 and 6 base GT sequences (Table 7).

TABLE 7

% inhibition of MCF-7 human breast cancer cell proliferation

| SEQUENCE | % INHIBITION |
|---|---|
| TGT-(TG)T SEQ ID NO:7-(3 bases) | −6 |
| GTG-(GT)G SEQ ID NO:8-(3 bases) | 18 |
| TGTGTG-(TG)$_3$ SEQ ID NO:9-(6 bases) | 6 |
| GTGTGT-(GT)$_3$ SEQ ID NO:10-(6 bases) | 31 |
| TTTGTT-TT(TG)$_1$TT SEQ ID NO:23-(6 bases) | 7 |
| GGTGGG-GG(TG)$_1$GG SEQ ID NO:24-(6 bases) | 41 |
| GGGTGG-GG(TG)$_1$GG SEQ ID NO:25-(6 bases) | 41 |
| TTGTTT-TT(GT)$_1$TT SEQ ID NO:26-(6 bases) | 20 |

As shown in Table 7, 6 and 7 base GT sequences inhibited MCF-7 cell proliferation.

EXAMPLE 7

Inhibition of PC-3 Human Prostate Cancer Cell Proliferation

PC-3 prostate cancer cells are a p53 mutated, androgen-independent human solid tumor model. PC-3 cells ($5\times10^5$ cells/ml) were incubated with 3 and 6 base GT sequences (Table 8).

TABLE 8

% inhibition of PC-3 human prostate cancer cell proliferation

| SEQUENCE | % INHIBITION |
|---|---|
| TGT-(TG)T SEQ ID NO:7-(3 bases) | 8 |
| GTG-(GT)G SEQ ID NO:8-(3 bases) | 13 |
| TGTGTG(TG)$_3$ SEQ ID NO:9-(6 bases) | 16 |
| GTGTGT-(GT)$_3$ SEQ ID NO:10-(6 bases) | 37 |
| TTTGTT-TT(TG)$_1$TT SEQ ID NO:23-(6 bases) | 14 |
| GGTGGG-GG(TG)$_1$GG SEQ ID NO:24-(6 bases) | 26 |
| GGGTGG-GG(GT)$_1$GG SEQ ID NO:25-(6 bases) | 38 |
| TTGTTT-TT(GT)$_1$TT SEQ ID NO:26-(6 bases) | 18 |

As shown in Table 8, 3 and 6 base GT sequences inhibited PC-3 cell proliferation.

EXAMPLE 8

Inhibition of LNCaP Human Prostate Cancer Cell Proliferation

LNCaP prostate cancer cells are a TGF-beta 1 receptor negative, androgen-independent, metastatic human solid tumor model. LNCaP cells ($5\times10^5$ cells/ml) were incubated with 6 base GT sequences (Table 9).

TABLE 9

% inhibition of LNCaP human prostate cancer cell proliferation

| SEQUENCE | % INHIBITION |
|---|---|
| TGTGTG-(TG)$_3$ SEQ ID NO:9-(6 bases) | −9 |
| GTGTGT-(GT)$_3$ SEQ ID NO:10-(6 bases) | −4 |
| TTTGTT-TT(TG)TT SEQ ID NO:23-(6 bases) | 14 |
| GGTGGG-GG(TG)GG SEQ ID NO:24-(6 bases) | 17 |
| GGGTGG-GG(GT)GG SEQ ID NO:25-(6 bases) | 18 |
| TTGTTT-TT(GT)TT SEQ ID NO:26-(6 bases) | 22 |

As shown in Table 9, 6 base GT sequences inhibited LNCaP cell proliferation.

EXAMPLE 9

Inhibition of THP-1 Human Acute Monocytic Leukemia Cell Proliferation

THP-1 acute monocytic leukemia cells are a p53 null human suspension tumor model. THP-1 cells (1.6×10$^6$ cells/ml) were incubated with 6 base GT sequences (Table 10).

TABLE 10

% inhibition of THP-1 human acute monocytic leukemia cell proliferation

| SEQUENCE | % INHIBITION |
|---|---|
| TGTGTG-(TG)$_3$ SEQ ID NO:9-(6 bases) | 0 |
| GTGTGT-(GT)$_3$ SEQ ID NO:10-(6 bases) | 11 |
| TTTGTT-TT(TG)$_1$TT SEQ ID NO:23-(6 bases) | 8 |
| GGTGGG-GG(TG)$_1$GG SEQ ID NO:24-(6 bases) | 6 |
| GGGTGG-GG(GT)$_1$GG SEQ ID NO:25-(6 bases) | 15 |
| TTGTTT-TT(GT)$_1$TT SEQ ID NO:26-(6 bases) | 1 |

As shown in Table 10, 6 base GT sequences inhibited THP-1 cell proliferation.

EXAMPLE 10

Inhibition of OVCAR-3 Human Ovarian Cancer Cell Proliferation

OVCAR-3 ovarian cancer cells are a p53 mutated, p21/waf-1/Cip deleted, metastatic human solid tumor model. OVCAR-3 cells (5×10$^5$ cells/ml) were incubated with 2, 6 and 18 base GT sequences and with a 6 base AGT sequence (Table 11).

TABLE 11

% inhibition of OVCAR-3 human ovarian cancer cell proliferation

| SEQUENCE | % INHIBITION |
|---|---|
| TG-(TG)$_1$ SEQ ID NO:51-(2 bases) | 23 |
| TTAGGG-TT(AG)$_1$GG SEQ ID NO:49-(6 bases) | 15 |
| GTGTGTGTGTGTGTGTGT-(GT)$_9$ SEQ ID NO:18-(18 bases) | 10 |
| GGGTGG-GG(GT)$_1$GG SEQ ID NO:25-(6 bases) | 15 |

As shown in Table 11, 2, 6 and 18 base GT sequences and a 6 base AGT sequence inhibited OVCAR-3 cell proliferation.

EXAMPLE 11

Inhibition of SK-OV-3 Human Ovarian Cancer Cell Proliferation

SK-OV-3 ovarian cancer cells are a p53 mutated, p21/waf-1/Cip deleted, p15$^{ink4B}$ deleted, p$_{16ink4}$ deleted, metastatic human solid tumor model. SK-OV-3 cells (5×10$^5$ cells/ml) were incubated with 2, 6 and 18 base GT sequences (Table 12).

TABLE 12

% inhibition of SK-OV-3 human ovarian cancer cell proliferation

| SEQUENCE | % INHIBITION |
|---|---|
| TG-(TG)$_1$ SEQ ID NO:51-(2 bases) | 18 |
| TTAGGG-TT(AG)$_1$GG SEQ ID NO:49-(6 bases) | 11 |
| GTGTGTGTGTGTGTGTGT-(GT)$_9$ SEQ ID NO:18-(18 bases) | 6 |
| GGGTGG-GG(GT)$_1$GG SEQ ID NO:25-(6 bases) | 12 |

As shown in Table 12, 2, 6 and 18 base GT sequences inhibited SK-OV-3 cell proliferation.

EXAMPLE 12

Inhibition of Cell Proliferation by Phosphodiester and Phosphorothioate Sequences Modification of natural phosphodiester sequences by substitution of a sulfur atom for a nonbridging oxygen atom on one or more of the phosphate groups has been reported to increase the stability of oligonucleotide sequences to endonucleases in biological fluids and cells (Crooke et al. Anticancer Drugs 6:609, 1991).

Jurkat human leukemia T cells (Table 13), LNCaP human prostate cancer cells (5×10$^5$ cells/ml) (Table 14) and MCF-7 human breast cancer cells (5×10$^5$ cells/ml) (Table 15) were incubated with 6 base GT sequences, having either oxygen (phosphodiester) or sulfur (phosphorothioate) as a nonbridging atom on the phosphate group.

TABLE 13

% inhibition of Jurkat human leukemia T cell proliferation

| | % INHIBITION | |
|---|---|---|
| SEQUENCE | PHOSPHODIESTER | PHOSPHOROTHIOATE |
| TGTGTG-(TG)$_3$ (6 bases) SEQ ID NO:9 phosphodiester; phosphorothioate | 37 | −17 |
| GTGTGT-(GT)$_3$ (6 bases) SEQ ID NO:10 phosphodiester; phosphorothioate | 44 | 0 |
| TTTGTT-TT(TG)$_1$TT (6 bases) SEQ ID NO:23 phosphodiester; phosphorothioate | 31 | 4 |
| GGTGGG-GG(TG)$_1$GG (6 bases) SEQ ID NO:24 phosphodiester; phosphorothioate | 48 | 6 |
| GGGTGG-GG(GT)$_1$GG (6 bases) SEQ ID NO:25 phosphodiester; phosphorothioate | 60 | 0 |
| TTGTTT-TT(GT)$_1$TT (6 bases) SEQ ID NO:26 phosphodiester; phosphorothioate | 34 | 0 |

TABLE 14

% inhibition of LNCaP human prostate cancer cell proliferation

| | % INHIBITION | |
|---|---|---|
| SEQUENCE | PHOSPHODIESTER | PHOSPHOROTHIOATE |
| TGTGTG-(TG)$_3$ (6 bases) SEQ ID NO:9 phosphodiester; phosphorothioate | −9 | −16 |
| GTGTGT-(GT)$_3$ (6 bases) SEQ ID NO:10 phosphodiester; phosphorothioate | −4 | −20 |
| TTTGTT-TT(TG)$_1$TT (6 bases) SEQ ID NO:23 phosphodiester; phosphorothioate | 14 | −11 |
| GGTGGG-GG(TG)$_1$GG (6 bases) SEQ ID NO:24 phosphodiester; phosphorothioate | 17 | −17 |
| GGGTGG-GG(GT)$_1$GG (6 bases) SEQ ID NO:25 phosphodiester; phosphorothioate | 18 | −8 |
| TTGTTT-TT(GT)$_1$TT (6 bases) SEQ ID NO:26 phosphodiester; phosphorothioate | 22 | −1 |

TABLE 15

% inhibition of MCF-7 human breast cancer cell proliferation

| | % INHIBITION | |
|---|---|---|
| SEQUENCE | PHOSPHODIESTER | PHOSPHOROTHIOATE |
| TGTGTG-(TG)$_3$ (6 bases) SEQ ID NO:9 phosphodiester; phosphorothioate | 6 | 6 |
| GTGTGT-(GT)$_3$ (6 bases) SEQ ID NO:10 phosphodiester; phosphorothioate | 31 | 12 |
| TTTGTT-TT(TG)$_1$TT (6 bases) SEQ ID NO:23 phosphodiester; phosphorothioate | 7 | 8 |
| GGTGGG-GG(TG)$_1$GG (6 bases) SEQ ID NO:24 phosphodiester; phosphorothioate | 41 | 12 |
| GGGTGG-GG(GT)$_1$GG (6 bases) SEQ ID NO:25 phosphodiester; phosphorothioate | 41 | 12 |
| TTGTTT-TT(GT)$_1$TT (6 bases) SEQ ID NO:26 phosphodiester; phosphorothioate | 20 | 6 |

As shown in Tables 13, 14 and 15, 6 base GT-phosphodiester sequences inhibited Jurkat T, LNCaP and MCF-7 cell proliferation more effectively than 6 base GT-phosphorothioate sequences.

EXAMPLE 13

Inhibition of Cell Proliferation by Mixed Phosphodiester and Phosphorothioate Sequences Jurkat human leukemia T cells (Table 16) and MCF-7 human breast cancer cells ($5'10^5$ cells/ml) (Table 17) were incubated with the 6 base GT SEQ ID NO:25, wherein either oxygen (phosphodiester) or sulfur (phosphorothioate) was the nonbridging atom on the phosphate group.

As shown in Tables 16 and 17, substitution of a sulfur atom for a nonbridging oxygen atom on one or more phosphate groups of 6 base GT SEQ ID NO:25 resulted in a significant decrease in inhibition of Jurkat T and MCF-7 cell proliferation.

EXAMPLE 14

Inhibition of Murine Cancer Cell Proliferation

EL-4 murine lymphoma T cells are a suspension tumor model. EL-4 murine lymphoma T cells were incubated with 6, 18, 27 and 33 base GT sequences and with a 15 base ACG sequence (Table 18).

TABLE 16

% inhibition of Jurkat human leukemia T cell proliferation

| SEQUENCE* | % INHIBITION |
|---|---|
| $G_oG_oG_oT_oG_oG_o$-$G_oG_o(G_oT_o)_1G_oG_o$ (oxygen atom 1 to 6) SEQ ID NO:25-(6 bases) | 60 |
| $G_oG_oG_sT_oG_oG_o$-$G_oG_o(G_sT_o)_1G_oG_o$ (oxygen atom 1,2,4,5,6; sulfur atom 3) SEQ ID NO:25-(6 bases) | 17 |
| $G_oG_oG_oT_sG_oG_o$-$G_oG_o(G_oT_s)_1G_oG_o$ (oxygen atom 1,2,3,5,6; sulfur atom 4) SEQ ID NO:25-(6 bases) | 12 |
| $G_oG_oG_sT_sG_oG_o$-$G_oG_o(G_sT_s)_1G_oG_o$ (oxygen atom 1,2,5,6; sulfur atom 3,4) SEQ ID NO:25-(6 bases) | 13 |
| $G_sG_oG_oT_oG_oG_s$-$G_sG_o(G_oT_o)_1G_oG_s$ (oxygen atom 2,3,4,5; sulfur atom 1,6) SEQ ID NO:25-(6 bases) | 16 |
| $G_oG_sG_oT_oG_sG_o$-$G_oG_s(G_oT_o)_1G_sG_o$ (oxygen atom 1,3,4,6; sulfur atom 2,5) SEQ ID NO:25-(6 bases) | 11 |
| $G_sG_sG_oT_oG_sG_s$-$G_sG_s(G_oT_o)_1G_sG_s$ (oxygen atom 3,4; sulfur atom 1,2,5,6) SEQ ID NO:25-(6 bases) | −13 |
| $G_sG_sG_sT_sG_sG_s$-$G_sG_s(G_sT_s)_1G_sG_s$ (sulfur atom 1 to 6) SEQ ID NO:25-(6 bases; phosphorothioate) | 0 |

*Note:
"o" represents an oxygen atom and "s" represents a sulfur atom on the phosphate group

TABLE 17

% inhibition of MCF-7 human breast cancer cell proliferation

| SEQUENCE* | % INHIBITION |
|---|---|
| $G_oG_oG_oT_oG_oG_o$-$G_oG_o(G_oT_o)_1G_oG_o$ (oxygen atom 1 to 6) SEQ ID NO:25-(6 bases; phosphodiester) | 41 |
| $G_oG_oG_sT_oG_oG_o$-$G_oG_o(G_sT_o)_1G_oG_o$ (oxygen atom 1,2,4,5,6; sulfur atom 3) SEQ ID NO:25-(6 bases) | 12 |
| $G_oG_oG_oT_sG_oG_o$-$G_oG_o(G_oT_s)_1G_oG_o$ (oxygen atom 1,2,3,5,6; sulfur atom 4) SEQ ID NO:25-(6 bases) | 0 |
| $G_oG_oG_sT_sG_oG_o$-$G_oG_o(G_sT_s)_1G_oG_o$ (oxygen atom 1,2,5,6; sulfur atom 3,4) SEQ ID NO:25-(6 bases) | 43 |
| $G_sG_oG_oT_oG_oG_s$-$G_sG_o(G_oT_o)_1G_oG_s$ (oxygen atom 2,3,4,5; sulfur atom 1,6) SEQ ID NO:25-(6 bases) | 12 |
| $G_oG_sG_oT_oG_sG_o$-$G_oG_s(G_oT_o)_1G_sG_o$ (oxygen atom 1,3,4,6; sulfur atom 2,5) SEQ ID NO:25-(6 bases) | 13 |
| $G_sG_sG_oT_oG_sG_s$-$G_sG_s(G_oT_o)_1G_sG_s$ (oxygen atom 3,4; sulfur atom 1,2,5,6) SEQ ID NO 25-(6 bases) | −3 |
| $G_sG_sG_sT_sG_sG_s$-$G_sG_s(G_sT_s)_1G_sG_s$; (sulfur atom 1 to 6) SEQ ID NO:25 (6 bases; phosphorothioate) | 12 |

*Note:
"o" represents an oxygen atom and "s" represents a sulfur atom on the phosphate group.

TABLE 18

% inhibition of EL-4 murine T lymphoma cell proliferation

| SEQUENCE | % INHIBITION |
|---|---|
| GGGTGG-GG(GT)$_1$GG<br>SEQ ID NO:25-(6 bases) | 4 |
| GGGTGG-GG(GT)$_1$GG<br>SEQ ID NO:25-(6 bases phosphorothioate) | −8 |
| GTGTGTGTGTGTGTGTGTGTGTGTGTG-(G$_1$T)$_{13}$G<br>SEQ ID NO:1-(27 bases) | 1 |
| GTGTGTTTGGTGGTTTTGTTTGTTGTTTTTTG<br>SEQ ID NO:66-(33 bases) | −1 |
| AACCACAAGCCCAAC<br>SEQ ID NO:67-(15 bases) | −6 |
| GTGTGT-(GT)$_3$<br>SEQ ID NO:10-(6 bases) | −2 |
| GTGTGTGTGTGTGTGTGT-(GT)$_9$<br>SEQ ID NO:18-(18 bases) | −2 |

As shown in Table 18, 6, 18, 27 and 33 base GT sequences and a 15 base ACG sequence did not inhibit EL-4 murine cell proliferation.

A20 murine leukemia B cells are a suspension tumor model. A20 murine leukemia B cells were incubated with 6 base GT sequences (Table 19).

TABLE 19

% inhibition of A20 murine B leukemia cell proliferation

| SEQUENCE | % INHIBITION |
|---|---|
| TGTGTG-(TG)$_3$<br>SEQ ID NO:9-(6 bases) | 22 |
| GTGTGT-(GT)$_3$<br>SEQ ID NO:10-(6 bases) | 9 |
| TTTGTT-TT(TG)$_1$TT<br>SEQ ID NO:23-(6 bases) | 5 |
| GGTGGG-GG(TG)$_1$GG<br>SEQ ID NO:24-(6 bases) | 9 |
| GGGTGG-GG(GT)$_1$GG<br>SEQ ID NO:25-(6 bases) | 11 |
| TTGTTT-TT(GT)$_1$TT<br>SEQ ID NO:26-(6 bases) | 15 |

As shown in Table 19, 6 base GT sequences inhibited proliferation of A20 murine B leukemia cells.

EXAMPLE 15

Inhibition of Canine Cancer Cell Proliferation

D-17 canine osteosarcoma cells and CF-51 canine mammary gland cancer cells are solid tumor models. D-17 canine osteosarcoma cells (5'10$^5$ cells/ml) (Table 20) and CF-51 canine mammary gland cancer cells (5'10$^5$ cells/ml) (Table 21) were incubated with 6, 9, 17, 27 and 33 base GT-sequences and with a 15 base ACG sequence.

TABLE 20

% inhibition of D-17 canine osteosarcoma cell proliferation

| SEQUENCE | % INHIBITION |
|---|---|
| GGGTGG-GG(GT)$_1$GG<br>SEQ ID NO:25-(6 bases) | 18 |
| GTGTGTGTGTGTGTGTGTGTGTGTGTG-(GT)$_{13}$G<br>SEQ ID NO:1-(27 bases) | 23 |
| GTGTGTTTGGTGGTTTTGTTTGTTGTTTTTTG<br>SEQ ID NO:66-(33 bases) | 23 |

TABLE 20-continued

% inhibition of D-17 canine osteosarcoma cell proliferation

| SEQUENCE | % INHIBITION |
|---|---|
| AACCACAAGCCCAAC<br>SEQ ID NO:67-(15 bases) | 20 |
| GTGTGT-(GT)$_3$<br>SEQ ID NO:10-(9 bases) | 15 |
| TGTGTGTGTGTGTGTGT-(TG)$_8$T<br>SEQ ID NO: 17-(17 bases) | 8 |

TABLE 21

% inhibition of CF-51 canine mammary gland cancer cell proliferation

| SEQUENCE | % INHIBITION |
|---|---|
| GGGTGG-GG(GT)$_1$GG<br>SEQ. ID NO:25-(6 bases) | 14 |
| GTGTGTGTGTGTGTGTGTGTGTGTGTG-(GT)$_{13}$G<br>SEQ ID NO:1-(27 bases) | 23 |
| GTGTGTTTGGTGGTTTTGTTTGTTGTTTTTTG<br>SEQ ID NO:66-(33 bases) | 23 |
| AACCACAAGCCCAAC<br>SEQ ID NO:67-(15 bases) | 20 |
| GTGTGT-(GT)$_3$<br>SEQ ID NO:10-(9 bases) | 15 |
| TGTGTGTGTGTGTGTGT-(TG)$_8$T<br>SEQ ID NO:17-(17 bases) | 8 |

As shown in Tables 20 and 21, 6, 9, 17, 27 and 33 base GT sequences and a 15 base ACG sequence inhibited both D-17 and CF-51 canine cell proliferation.

EXAMPLE 16

Inhibition of Cancer Cell Proliferation

Inhibition of human, murine and canine cancer cell proliferation by 6 base GT SEQ ID NO:25 is summarized in Table 22.

TABLE 22

% inhibition of human, murine and canine cancer cell proliferation

| CELLS | GG(GT)$_1$GG (SEQ ID NO:25) |
|---|---|
| HUMAN Jurkat | 60 |
| HUMAN PC-3 | 38 |
| HUMAN MCF-7 | 41 |
| HUMAN HL-60 | 35 |
| HUMAN OVCAR-3 | 14 |
| HUMAN LNCaP | 18 |
| HUMAN SK-OV-3 | 12 |
| HUMAN THP-1 | 15 |
| MURINE EL-4 | 1 |
| MURINE A20 | 11 |
| MURINE L-1210 | 8 |

TABLE 22-continued

% inhibition of human, murine and canine cancer cell proliferation

| CELLS | GG(GT)₁GG (SEQ ID NO:25) |
|---|---|
| CANINE D17 | 18 |
| CANINE CF-51 | 14 |

As shown in Table 22, human cancer cells are more sensitive than canine cancer cells and murine cancer cells to inhibition of proliferation by 6 base GT SEQ ID NO:25.

EXAMPLE 17

Synergistic Effect of Two 6 Base GT Sequences on Inhibition of Proliferation

Jurkat human leukemia T cells were incubated with suboptimal concentrations (5.0 µg/ml) of 6 base GT sequences (Table 23).

TABLE 23

% inhibition of Jurkat human leukemia T cell proliferation

| SEQUENCE | % INHIBITION |
|---|---|
| GGGTGG-GG(GT)₁GG SEQ ID NO:25-(6 bases) | 5 |
| TTGTTT-TT(GT)₁GG SEQ ID NO:26-(6 bases) | −2 |
| GG(GT)₁GG + TT(GT)₁GG SEQ ID NO:25 + SEQ ID NO:26 | 14 |
| TGGTTG-TG(GT)₁TG SEQ ID NO:29-(6 bases) | −1 |
| TGGTTG-TG(GT)₁TG SEQ ID NO:10-(6 bases) | 2 |
| TG(GT)₁TG + TG(GT)₁TG SEQ ID NO:29 + SEQ ID NO:10 | 9 |
| GGTTGG-GG(TT)₁GG SEQ ID NO:41-(6 bases) | 4 |
| TTGTGG-TT(GT)₁GG SEQ ID NO:39-(6 bases) | 4 |
| GG(TT)₁GG + TT(GT)₁GG SEQ ID NO:41 + SEQ ID NO:39 | 18 |

As shown in Table 23, the simultaneous use of two 6 base GT sequences had a synergistic effect on inhibition of Jurkat T cell proliferation.

EXAMPLE 18

Potentiation of Antineoplastic Effect of Chemotherapeutic Drugs

Jurkat human leukemia T cells were incubated with 1.0 µg/ml of 6 base GT SEQ ID NO:25 and of 27 base GT SEQ ID NO:1 in the presence of 0, 0.1, 1.0 or 10.0 µg/ml of 5-fluorouracil or cisplatin (Table 24). 5-fluorouracil is an antimetabolite that interferes with DNA and RNA synthesis. Cisplatin is an alkylating agent that cross-links DNA and inhibits DNA precursors.

TABLE 24

% inhibition of Jurkat human leukemia T cell proliferation

| | % INHIBITION | | | |
|---|---|---|---|---|
| SEQUENCES | 0.0 | 0.1 | 1.0 | 10.0 |
| | 5-Fluorouracil (µg/ml) | | | |
| 5-Fluorouracil | 0 | 3 | 14 | 38 |
| GG(GT)₁GG-(6 bases) SEQ ID NO:25 at 1.0 µg/ml | 0 | 10 | 21 | 40 |
| (GT)₁₃G-(27 bases) SEQ ID NO:1 at 1.0 µg/ml | 3 | 15 | 25 | 41 |
| | Cisplatin (µg/ml) | | | |
| Cisplatin | 0 | 7 | 29 | 73 |
| GG(GT)₁GG-(6 bases) SEQ ID NO:25 at 1.0 µg/ml | 0 | 14 | 38 | 76 |
| (GT)₁₃G-(27 bases) SEQ ID NO:1 at 1.0 µg/ml | 3 | 18 | 35 | 76 |

As shown in Table 24, 6 base GT SEQ ID NO:25 and 27 base GT SEQ ID NO:1 potentiated the antineoplastic effect of 0.1 and 1.0 µg/ml of 5-fluorouracil on Jurkat T cell proliferation and GT SEQ ID NO:25 potentiated the antineoplastic effect of 0.1 and 1.0 µg/ml cisplatin on Jurkat T cell proliferation.

MCF-7 human breast cancer cells ($5 \times 10^5$ cells/ml) were incubated with 1.0 µg/ml of 6 base GT SEQ ID NO:25 and of 27 base GT SEQ ID NO:1 in the presence of 0, 0.1, 1.0 or 10.0 µg/ml of 5-fluorouracil or tamoxifen (Table 25). Tamoxifen is an estrogen antagonist.

TABLE 25

% inhibition of MCF-7 human breast cancer cell proliferation

| | % INHIBITION | | | |
|---|---|---|---|---|
| SEQUENCES | 0.0 | 0.1 | 1.0 | 10.0 |
| | 5-Fluorouracil (µg/ml) | | | |
| 5-Fluorouracil | 0 | 13 | 28 | 28 |
| GG(GT)₁GG-(6 bases) SEQ ID NO:25 at 1.0 µg/ml | 6 | 24 | 36 | 33 |
| (G₁T)₁₃G (27 bases) SEQ ID NO:1 at 1.0 µg/ml | 8 | 24 | 35 | 33 |
| | Tamoxifen (µg/ml) | | | |
| Tamoxifen | 0 | 10 | 18 | 15 |
| GG(GT)₁GG-(6 bases) SEQ ID NO:25 at 1.0 µg/ml | 6 | 21 | 24 | 31 |
| (GT)₁₃G-(27 bases) SEQ ID NO:1 at 1.0 µg/ml | 8 | 19 | 24 | 20 |

As shown in Table 25, 6 base SEQ ID NO:25 potentiated the antineoplastic effect of 0.1 µg/ml 5-flurouracil and of 0.1 µg/ml tamoxifen on MCF-7 cell proliferation. Twenty-seven base SEQ ID NO:1 did not potentiate the antineoplastic activity of 5-fluorouracil or of tamoxifen on MCF-7 cell proliferation.

EXAMPLE 19

Inhibition of Proliferation by Repeats of 6 Base GT SEQ ID NO:25

Jurkat human leukemia T cells were incubated with 1, 2, 3 and 4 repeats of 6 base GG(GT)1GG (SEQ ID NO:25) (Table 26).

TABLE 26

% inhibition of Jurkat human leukemia T cell proliferation

| SEQUENCE | % Inhibition |
|---|---|
| GGGTGG-GG(GT)₁GG<br>SEQ ID NO:25-(6 bases) | 60 |
| GGGTGGGGGTGG-[GG(GT)₁GG]₂<br>SEQ ID NO:68-(12 bases) | 18 |
| GGGTGGGGGTGGGGGTGG-[GG(GT)₁GG]₃<br>SEQ ID NO:69-(18 bases) | 5 |
| GGGTGGGGGTGGGGGTGGGGGTGG-[GG(GT)₁GG]₄<br>SEQ ID NO:70-(24 bases) | 13 |

As shown in Table 26, inhibition of Jurkat T cell proliferation was 60% with 6 base GT SEQ. ID NO:25 and decreased with 12 base GT SEQ ID NO:68, 18 base GT SEQ ID NO:69 and 24 base GT SEQ ID NO:70. The melting temperature (Tm) of 6 base GT SEQ ID NO:25 was 2.5° C. and increased to 56.8° C. with GT SEQ ID NO:68, to 76.3° C. with GT SEQ ID NO:69 and to 86.3° C. with GT SEQ ID NO:70.

EXAMPLE 20

Inhibition of Proliferation by *Bacillus* Calmette-guerin (BCG) Derived Sequences BCG derived sequences are reported to inhibit tumor growth in vivo (Kataoka et al. Jpn. J. Cancer Res. 83:244, 1992). In addition, A-2 (SEQ ID NO:72) and BCG A-4 (SEQ ID NO:74), when pre-mixed with IMC cells and injected into CDF-1 mice, are reported to inhibit IMC tumor growth by 88% and 37% respectively.

Jurkat human leukemia T cells were incubated with 45 base sequences derived from BCG (Table 27).

TABLE 27

% inhibition of Jurkat human leukemia T cell proliferation

| SEQUENCE | % INHIBITION |
|---|---|
| BCG A-1<br>AAAGAGGGGCATGACCCGGTGC<br>GGGGCTTCTTGCACTCGGCATAG<br>SEQ ID NO:71 (45 bases) | 6 |
| BCG A-2<br>AAAGAAGTGGGGTGCCCCCAC<br>GATCACCAACGATGGTGTGTCCA<br>SEQ ID NO:72-(45 bases) | 19 |
| BCG A-3<br>TCCATCGCCAAGGAGATCGAGC<br>TGGAGGATCGTACGAGAAGATC<br>SEQ ID NO:73-(45 bases) | 24 |

TABLE 27-continued

% inhibition of Jurkat human leukemia T cell proliferation

| SEQUENCE | % INHIBITION |
|---|---|
| BCG A-4<br>ACCGATGACGTCGCCGGTGACG<br>GCAACACGACGGCCACCGTGCTG<br>SEQ ID NO:74-(45 bases) | 9 |
| BCG A-6<br>ACGAGACCACCATCGTCGAGGG<br>CGCCGGTGACACCGACGCCATCG<br>SEQ ID NO:75-(45 bases) | 21 |
| BCG A-7<br>GCCGAGAAGGTGCGCAACCTGC<br>CGGCTGGCCACGGACTGAACGCT<br>SEQ ID NO:76-(45 bases) | 4 |
| BCG M-3<br>ACGCCGACGTCGTCTGTGGTGG<br>GGTGTCTACCGCCAACGCGACGG<br>SEQ ID NO:77-(45 bases) | 22 |
| BCG ALPHA-1<br>CGACTACAACGGCTGGGATATC<br>AACACCCCGGCGTTCGAGTGGTA<br>SEQ ID NO:78-(45 bases) | 10 |

As shown in Table 27, BCG derived sequences inhibited Jurkat T cell proliferation ≦24%.

EXAMPLE 21

Induction of Cell Cycle Arrest

Cell cycle stage was determined using a CYCLETEST™ PLUS DNA commercial kit (Becton Dickinson). Briefly, nuclei from cells were obtained by dissolving the cell membrane in a nonionic detergent, eliminating the cell cytoskeleton and nuclear proteins with trypsin, digesting the cellular RNA with RNase and stabilizing the nuclear chromatin with spermine. Propidium iodide was added to the cell nuclei and their fluorescence was analyzed in a flow cytometer equipped with electronic doublet discrimination capability (FACSCalibur, Becton Dickinson, San Jose, Calif.). Accumulation of cells in $G_0$/G1, early S (SE), mid S (SM), late S (SL) or $G_2$/M phases of the cell cycle was analyzed using MODFIT LT software (Verity Software House Inc., Topsham, Mass.).

Exponentially growing Jurkat human leukemia T cells (Table 28) and MCF-7 human breast cancer cells ($5 \times 10^5$ cells/ml) (Table 29) were incubated for 24 h with 2, 6, 15, 18, 27 and 45 base sequences containing A, C, G and T. The cells were collected and centrifuged and cell cycle stage was determined.

TABLE 28

Induction of cell cycle arrest in Jurkat T human leukemia cells

| | % of cells in phase: | | | | |
|---|---|---|---|---|---|
| | $G_0/G_1$ | SE | SM | SL | $G_2$/M Arrest* |
| Untreated cells | 31.4 | 19.1 | 14.3 | 11.6 | 23.6 None |
| GG(GT)₁GG<br>SEQ ID NO:25-(6 bases) | 28.5 | 46.3 | 14.6 | 10.7 | 0.0 End SE |
| TT(GT)₁TT<br>SEQ ID NO:26-(6 bases) | 32.6 | 11.5 | 12.8 | 10.7 | 32.4 End $G_2$/M (weak) |

TABLE 28-continued

Induction of cell cycle arrest in Jurkat T human leukemia cells

| | % of cells in phase: | | | | | |
|---|---|---|---|---|---|---|
| | $G_0/G_1$ | SE | SM | SL | $G_2/M$ | Arrest* |
| GT(GT)$_1$GT SEQ ID NO:10-(6 bases) | 30.8 | 41.9 | 16.8 | 10.2 | 0.3 | End SE |
| AG(GT)$_1$GA SEQ ID NO:31-(6 bases) | 35.2 | 29.1 | 10.4 | 8.2 | 17.1 | Mid SE |
| GG(AA)$_1$GG SEQ ID NO:42-(6 bases) | 48.0 | 19.8 | 8.5 | 5.8 | 34.1 | End $G_0/G_1$ |
| GG(CC)$_1$GG SEQ ID NO:43 (6 bases) | 26.5 | 21.3 | 22.8 | 10.7 | 18.7 | End SM (weak) |
| GG(GT)$_1$GG SEQ ID NO:25-(6 bases phosphorothioate) | 34.9 | 14.8 | 15.0 | 10.6 | 24.7 | None |
| $(G_1T)_{13}G$ SEQ ID NO:1-(27 bases) | 40.6 | 35.6 | 14.2 | 9.3 | 0.3 | End SE |
| $(G_1T)_{13}G$ SEQ ID NO: 1-(27 bases phosphorothioate) | 33.7 | 17.6 | 13.2 | 11.0 | 24.5 | None |
| $(G_3T)_6G_3$ SEQ. ID NO:2-(27 bases) | 34.3 | 15.5 | 13.6 | 10.3 | 26.4 | None |
| $(G_5T)_4G_3$ SEQ ID NO:3-(27 bases) | 40.5 | 13.3 | 12.9 | 9.7 | 23.6 | None |
| $(G_7T)_3G_3$ SEQ ID NO:4-(27 bases) | 36.5 | 16.3 | 13.8 | 11.1 | 22.3 | None |
| AACCACAAGCCCAAC SEQ ID NO:67-(15 bases) | 39.6 | 13.5 | 12.8 | 9.5 | 24.6 | None |
| TT(AG)$_1$GG SEQ ID NO:49-(6 bases) | 24.6 | 37.2 | 19.5 | 5.9 | 12.8 | Mid SM |
| (GT)$_9$ SEQ ID NO:18-(18 bases) | 24.2 | 26.7 | 24.0 | 8.7 | 16.4 | Mid SM |
| BCG A-1 SEQ ID NO:71-(45 bases) | 19.8 | 31.7 | 22.5 | 14.0 | 12.0 | Mid SM |
| BGC A-3 SEQ ID NO:73-(45 bases) | 32.3 | 20.2 | 14.1 | 12.0 | 21.4 | None |
| TG SEQ ID NO:51-(2 bases) | 23.1 | 52.3 | 14.8 | 9.8 | 0.0 | End SE |

As shown in Table 28, in Jurkat T cells, 2, 6 and 27 base GT sequences induced arrest in the SE phase of the cell cycle, 6 base CG and AGT, 18 base GT aid 45 base BCG A-1 sequences induced arrest in the SM phase of the cell cycle and a 6 base AG sequence induced arrest in the $G_0/G_1$ phase of the cell cycle.

TABLE 29

Induction of cell cycle arrest in MCF-7 human breast cancer cells

| | % cells in phase: | | | | | |
|---|---|---|---|---|---|---|
| | $G_0/G_1$ | SE | SM | SL | $G_2/M$ | Arrest* |
| Untreated cells | 23.6 | 14.4 | 10.8 | 11.1 | 40.1 | None |
| GG(GT)$_1$GG SEQ ID NO:25- (6 bases) | 21.9 | 27.6 | 22.2 | 10.9 | 17.4 | End SM |
| TT(AG)$_1$GG SEQ ID NO:49- (6 bases) | 20.0 | 18.6 | 25.7 | 20.7 | 15.0 | Mid SM |
| (GT)$_9$ SEQ ID NO:18- (18 bases) | 25.3 | 31.6 | 16.9 | 10.5 | 15.7 | Mid SM |
| TG SEQ ID NO:51- (2 bases) | 17.2 | 36.4 | 13.4 | 14.1 | 17.9 | End SE |

As shown in Table 29, in MCF-7 cells, 2 and 6 base GT sequences induced arrest in the SE phase of the cell cycle, a 6 base AGT sequence and an 18 base GT sequence induced arrest in the SM phase of the cell cycle.

EXAMPLE 22

Induction of Cell Cycle Arrest by GT SEQ ID NO:25, AC SEQ ID NO:79 and GT SEQ ID NO:25+AC SEQ ID NO:79

Jurkat human cell leukemia T cells ($1 \times 10^6$ cells/ml) were incubated for 24 h with 6 base GT SEQ ID NO:25, complementary 6 base AC SEQ ID NO:79 and 6 base GT SEQ ID NO:25+6 base AC SEQ ID NO:79. GT SEQ ID NO:25 and AC SEQ ID NO:79 were hybridized by mixing the oligonucleotides (1:1) and heating for 10 minutes at 65° C. As controls, GT SEQ ID NO:25 and AC SEQ ID NO:79 were heated for 10 minutes at 65° C. (Table 30).

TABLE 30

Induction of cell cycle arrest in Jurkat human leukemia T cells

| | % cells in phase: | | | | | |
|---|---|---|---|---|---|---|
| | $G_0/G_1$ | SE | SM | SL | $G_2/M$ | Arrest |
| Untreated cells | 31.7 | 15.2 | 13.7 | 14.0 | 25.4 | None |
| GG(GT)$_1$GG SEQ ID NO:25- (6 bases) | 28.0 | 45.8 | 14.0 | 11.3 | 0.9 | End SE |
| CC(AC)$_1$CC SEQ ID NO:79- (6 bases) | 36.0 | 10.4 | 13.4 | 9.7 | 30.5 | None |
| GT(GT)$_1$GT + CC(AC)$_1$CC SEQ NO:25 + SEQ NO:79- (12 bases) | 35.0 | 13.0 | 10.1 | 8.7 | 33.2 | None |

As shown in Table 30, 6 base GT SEQ ID NO:25 induced arrest at the end of the SE phase of the cell cycle, whereas the complementary 6 base AC SEQ ID NO:79 had no effect on the cell cycle. Hybridization of GT SEQ ID NO:25 and AC SEQ ID NO:79 neutralized GT SEQ ID NO:25 induction of cell cycle arrest. These data demonstrate that to be effective, the sequences of the present invention must be single stranded.

EXAMPLE 23

Induction of Apoptosis

Redistribution of plasma membrane phosphatidylserine and release of nuclear matrix protein (NuMA) are charactersirics of cells undergoing apoptosis (Martinet al. J. Exp. Med., 182:1545, 1995; Miller et al. Biotechniques, 15:1042, 1993).

The redistribution of phosphatidylserine in the plasma membrane during apoptosis was measured by flow cytometry using FITC-conjugated annexin V (BD Pharmingen, San Diego, Calif.). NuMA release into the supernatant was determined using a commercial ELISA kit (Oncogen/Calbiochem, Cambridge, Mass.).

Jurkat human leukemia T cells were incubated with 50 µM of 3, 4, 5, 6 and 7 GT base sequences, a 5 base ACGT sequence, 6 base AG, GG, AGT and CGT sequences and a 7 base GG sequence. Table 31 shows % of cells in apoptosis (positive for phosphatidyl-serine/annexin V staining (PS/A-V)) and % NuMA released from the cells.

TABLE 31

Induction of apoptosis in Jurkat T cell leukemia cells

| SEQUENCE | % of cells in apoptosis (positive for PS/A-V staining) | % NuMA released (treated vs untreated cells) |
|---|---|---|
| Untreated cells | 4 | 0 |
| GG(GT)$_1$GG SEQ ID NO:2-(6 bases) | 27 | 69 |
| GG(GA)$_1$GG SEQ ID NO:45-(6 bases) | 27 | 74 |
| GG(GC)$_1$GG SEQ ID NO:46-(6 bases) | 16 | 11 |
| GG(GG)$_1$GG SEQ ID NO:44-(6 bases) | 5 | 0 |
| AA(GT)$_1$AA SEQ ID NO:27-(6 bases) | 20 | 56 |
| CC(GT)$_1$CC SEQ ID NO:28-(6 bases) | 6 | 0 |
| TT(GT)$_1$TT SEQ ID NO:26-(6 bases) | 14 | 23 |
| GT(GT)$_1$GT SEQ ID NO:10-(6 bases) | 33 | 90 |
| GG(GT)$_1$ SEQ ID NO:78-(4 bases) | 21 | 64 |
| (GT)$_1$GG SEQ ID NO:52-(4 bases) | 24 | 60 |
| G(GT)$_1$G SEQ ID NO:56-(4 bases) | 24 | 112 |
| (GT)$_1$G SEQ ID NO:8-(3 bases) | 21 | 97 |
| T(GT)$_1$ SEQ ID NO:7-(3 bases) | 10 | 35 |
| GG(GT)$_1$G SEQ ID NO:6-(5 bases) | 25 | 92 |
| G(GT)$_1$GG SEQ ID NO:60-(5 bases) | 25 | 120 |
| GG(GG)$_1$GGG SEQ ID NO:63-(7 bases) | 12 | 26 |
| GGG(GT)$_1$GG SEQ ID NO:62-(7 bases) | 30 | 123 |

TABLE 31-continued

Induction of apoptosis in Jurkat T cell leukemia cells

| SEQUENCE | % of cells in apoptosis (positive for PS/A-V staining) | % NuMA released (treated vs untreated cells) |
|---|---|---|
| CG(GT)$_1$A SEQ ID NO:80-(5 bases) | 6 | 9 |

As shown in Table 31, 3, 4, 5, and 6 base GT, AG, CG and AGT sequences induced apoptosis of Jurkat T cells. Five base ACGT and 6 base CGT and GG sequences did not induce apoptosis of Jurkat T cells.

EXAMPLE 24

Increase in Intracellular Calcium ($Ca^{2+}$)

Increases in intracellular calcium $(Ca^{2+})_i$ are reported to be associated with apoptosis induction (Lam et al. Mol. Endocrinol. 7:686, 1993). $(Ca^{2+})_i$ was followed using the fluorescent probe Fluo-3-AM (Cell Permaant, Molecular Probes, Inc., Eugene, Oreg.). An increase in Fluo-3-AM fluorescence is indicative of an increase in $(Ca^{2+})_i$.

Jurkat human leukemia T cells were incubated for 24 h with 6 base GT SEQ. NO:25. Cells were collected by centrifugation, suspended in PBS containing 1% FBS and loaded with 10 µM Fluo-3-AM for 1 h at 37° C. Cell fluorescence was measured at 488 nm excitation and 530 nm emission (FL1 detector). Data were analyzed on a FACS-CALIBUR using the program CellQUEST (Becton Dickinson).

As shown in FIG. 1, incubation of Jurkat T cells with 6 base GT SEQ ID NO:25 caused an 88% increase in cell fluorescence, indicative of an increase in $(Ca^{2+})_i$.

EXAMPLE 25

Induction of Apoptosis

Apoptosis can be initiated by ligands that bind to cell surface receptors including, but not limited to, Fas (CD95) and tumor necrosis factor (TNF). Fas binding to Fas Ligand and TNF binding to TNF Receptor 1 initiate intracellular signaling resulting in the activation of cysteine aspartyl proteases (caspases). Caspases initiate the lethal proteolytic cascade of apoptosis execution associated with nuclear DNA-fragmentation, release of nuclear matrix proteins (NuMA) and loss of cell substrate contact.

Jurkat human leukemia T cells ($1 \times 10^6$/ml) were incubated with 6 and 27 GT base sequences (Table 32). NuMA was determined as in Example 23.

TABLE 32

% NuMA release from Jurkat human leukemia T cells

| SEQUENCE | % NuMA RELEASED |
|---|---|
| GTGTGTGTGTGTGTGTGTGTGTGTGTG-(G$_1$T)$_{13}$G SEQ ID NO:1-(27 bases) | 22 |
| GGGTGGGTGGGTGGGTGGGTGGGTGGG-(G$_3$T)$_6$G$_3$ SEQ ID NO:2-(27 bases) | 49 |
| GGGGGTGGGGGTGGGGGTGGGGGTGGG-(G$_5$T)$_4$G$_3$ SEQ ID NO:3-(27 bases) | 139 |

TABLE 32-continued

% NuMA release from Jurkat human leukemia T cells

| SEQUENCE | % NuMA RELEASED |
|---|---|
| GGGGGGGTGGGGGGGTGGGGGGGTGGG-$(G_7T)_3G_3$ SEQ ID NO:4-(27 bases) | 90 |
| GGGTGG-GG$(GT)_1$GG SEQ ID NO:25-(6 bases) | 269 |

As shown in Table 32, % NuMA release with 6 base GT SEQ ID NO:25 was greater than % NuMA release with 27 base GT SEQ ID NOs:1, 2, 3 and 4.

EXAMPLE 26

Induction of Apoptosis by 6 Base GT SEQ ID NO:25 and 6 Base AC SEQ ID NO:79

Jurkat human cell leukemia T cells were incubated for 24 h with 6 base GT SEQ ID NO:25, complementary 6 base AC SEQ ID NO:79, and 6 base GT SEQ ID NO:25+6 base AC SEQ ID NO:79. GT SEQ ID NO:25 and AC SEQ ID NO:79 were hybridized by mixing the sequences (1:1) and heating for 10 minutes at 65° C. As controls, GT SEQ ID NO:25 and AC SEQ ID NO:79 were heated for 10 minutes at 65° C. (Table 33). Apoptosis was evaluated as in Example 23.

TABLE 33

Induction of apoptosis in Jurkat human leukemia T cells

| | % cells in apoptosis (positive for PS/A-V staining) | % NuMA released (untreated vs treated cells) |
|---|---|---|
| Untreated cells | 4 | 0 |
| GG$(GT)_1$GG SEQ ID NO:25-(6 bases) | 27 | 69 |
| CC$(AC)_1$CC SEQ ID NO:79-(6 bases) | 6 | 9 |
| GT$(GT)_1$GT + CC$(AC)_1$CC SEQ ID NO:25-(6 bases) + SEQ ID NO:79-(6 bases) | 5 | 9 |

As shown in Table 33, 6 base GT SEQ ID NO:25 induced apoptosis of Jurkat T cells, whereas the complementary AC SEQ ID NO:79 had no effect on apoptosis. Moreover, hybridization of GT SEQ ID NO:25 and AC SEQ ID NO:79 neutralized GT SEQ ID NO:25's induction of apoptosis. These data demonstrate that to be effective, the sequences of the present invention must be single stranded.

EXAMPLE 27

Inhibition of Proliferation, Cell Cycle Arrest and Induction of Apoptosis by GT-rich and AC-rich Sequences Derived from *Mycobacterium phlei*

Jurkat human leukemia T cells were incubated with GT-rich or AC-rich sequences derived from the murA gene of *Mycobacterium phlei* (GenBank: Accession Number X99776). Inhibition of proliferation was measured by the reduction of MTT as in Example 3, cell cycle arrest was detected by flow cytometry using propidium iodide as in Example 21 and apoptosis was evaluated by flow cytometry using annexin-V-FITC as in Example 23.

TABLE 34

Inhibition of proliferation, cell cycle arrest and induction of apoptosis in Jurkat cells

| SEQUENCE | % inhibition (proliferation) | % of cells in apoptosis | cell cycle arrest |
|---|---|---|---|
| AACCACAAGCCCAAC SEQ ID NO:67-(15 bases) | 0 | 4 | No |
| GTGTGTTTGGT SEQ ID NO:81-(11 bases) | 22 | 23 | G0/G1 |
| GGTTTTGTTTG SEQ ID NO:82-(11 bases) | 20 | 25 | End SE |
| TTGTTTTTTTTG SEQ ID NO:83-(11 bases) | 21 | 16 | SM |

As shown in Table 34, SEQ ID NOs: 81, 82 and 83, rich in GT, inhibited proliferation of, induced cell cycle arrest in and induced apoptosis of Jurkat T cells, whereas SEQ ID NO:15, rich in AC, did not inhibit proliferation of, induce cell cycle arrest in or induce apoptosis of Jurkat T cells.

EXAMPLE 28

Modulation of Caspase Activation by GT Sequences

Caspases recognize 3 major peptide substrate sequences: 1) Tyr-Val-Ala-Asp (YVAD, caspase-1, -4 and -5) (SEQ ID NO:84); 2) Asp-Glu-Val-Asp (DEVD, caspase-2, -3 and -7) (SEQ ID NO:85); and, 3) Ile-(Leu)-Glu-X-Asp (I(L)EXD; caspase-8 and -10) (SEQ ID NO:86) (Thornberry et al. J. Biol. Chem. 272:17907, 1997). Sequence recognition in a protein target results in a limited and specific proteolysis of the target as, in a first example, the modulation of caspase 7 activation by caspase 3 or, as in a second example, the degradation of structural protein targets including, but not limited to, lamins or, as in a third example, the activation of enzymes including, but not limited to, PARP.

$NH_2$-XXXD-COO-GT sequence constructs are generated by chemical conjugation of a chemically protected GT sequence or of a chemically protected AC sequence to a chemically protected peptide selected from the group consisting of $NH_2$-YVAD-COOH (SEQ ID NO:84), $NH_2$-DEVD-COOH (SEQ ID NO:85) and $NH_2$-IEGD-COOH (SEQ ID NO:87) using an oligonucleotide synthesized with a 5'-$C_2$ amide spacer arm and standard amide-carboxyl water soluble carbohexiimide conjugation techniques (Guy et al. J. Chromatography. B. Biomed. Sci. Appl. 706:149, 1998). Reactive carboxylate and reactive amine groups are deprotected subsequent to conjugation, Peptide-GT (hereinafter, PGT) sequence constructs including, but not limited to, $NH_2$-YVAD-COO-GT; $NH_2$-DEVD-COO-GT; and, $NH_2$-I(L)EXD-COO-GT are cleaved at the carboxylate function between D and the GT sequence by enzymes including, but not limited to, caspases, cancer metastasis associated enzymes, collagenase and metalloproteinases. Such cleavage results in the rebase of the caspase-activating GT sequence from the PGT. The resulting increase in intracellular caspase activity can, for example, enhance the therapeutic effect of chemotherapeutic agents in multidrug resistant cancer cells or the immune response to weakly antigenic stimuli.

To determine caspase activation, control and treated cells are washed, fixed, permeabilized and incubated with an FITC-conjugated antibody that recognizes the active form of the caspase (Pharmingen, San Diego, Calif.) using the conditions recommended by the manufacturer. Fluorescence associated with active caspase 3 is analyzed by flow cytometry on a FACSCALIBUR using the program CellQUEST (Becton Dickinson). Alternatively, caspase activation is determined calorimetrically using an assay based on the cleavage of a caspase-specific peptide conjugated to the color reporter molecule p-nitroanilide, which can be quantitated spectrophotometrically at a wavelength of 405 nm.

EXAMPLE 29

Activation of Caspase 3 by GT SEQ ID NOs: 66, 81, 82 and 83 and by AGC Sequence SEQ ID NO:67

Jurkat T cell leukemia cells were incubated for 72 h with 33 base GT SEQ ID NO:66; 11 base GT SEQ ID NO:81 (bases 1–11 of GT SEQ ID NO:66), 11 base GT SEQ ID NO:82 (bases 12–22 of GT SEQ ID NO:66), 11 base GT SEQ ID NO:83 (bases 23–33 of GT SEQ ID NO:66) and 15 base ACG SEQ ID NO:67. Active caspase 3 (17–22 kDa) was determined using FITC conjugated antibody (Clone: C92-605) as in Example 28.

Figure 2:
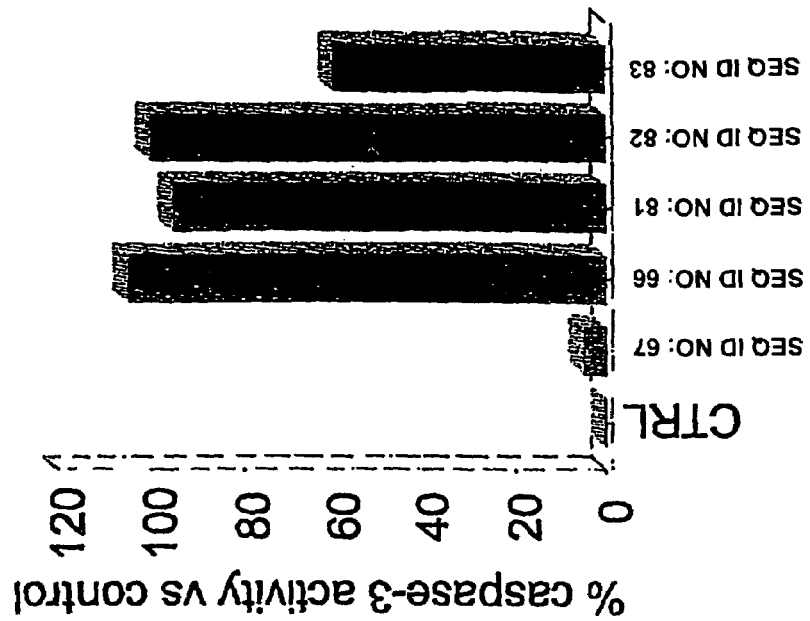
FIG. 2. Caspase 3 activation in Jurkat human T cell leukemia cells incubated without 0 µg/ml and 100 µg/ml of GT SEQ ID NOs:66, 67, 81, 82 and 83 measured cytometrically (A) and calorimetrically (B).
Figure 2:
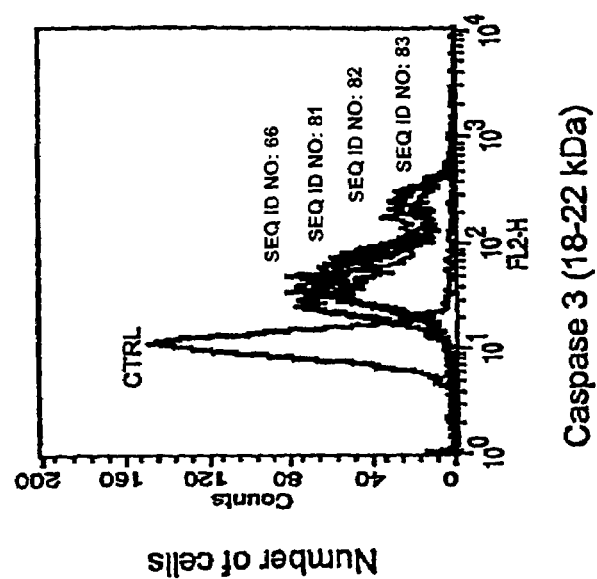

As shown in FIG. 2A, 33 base GT SEQ ID NO:66 and 11 base GT SEQ ID NOs:81, 82 and 83 each induced processing of inactive pro-caspase 3 to active caspase 3, whereas 15 base ACG SEQ ID NO:67 did not induce processing of inactive pro-caspase 3 to active caspase 3.

Caspase 3 activation also was determined calorimetrically as in Example 28. As As shown in FIG. 2B, caspase 3 activity in 33 base GT SEQ ID NO:66 and 11 base GT SEQ ID NOs:81, 82 and 83 treated cells was 105%, 77%, 100% and 60% greater than that in control cells, whereas in 15 base ACG SEQ ID NO:67 treated cells caspase 3 activation was approximately the same as in control cells.

EXAMPLE 30

Activation of Caspase 3 Activity by 6 Base GT SEQ ID NO:25

Figure 3:
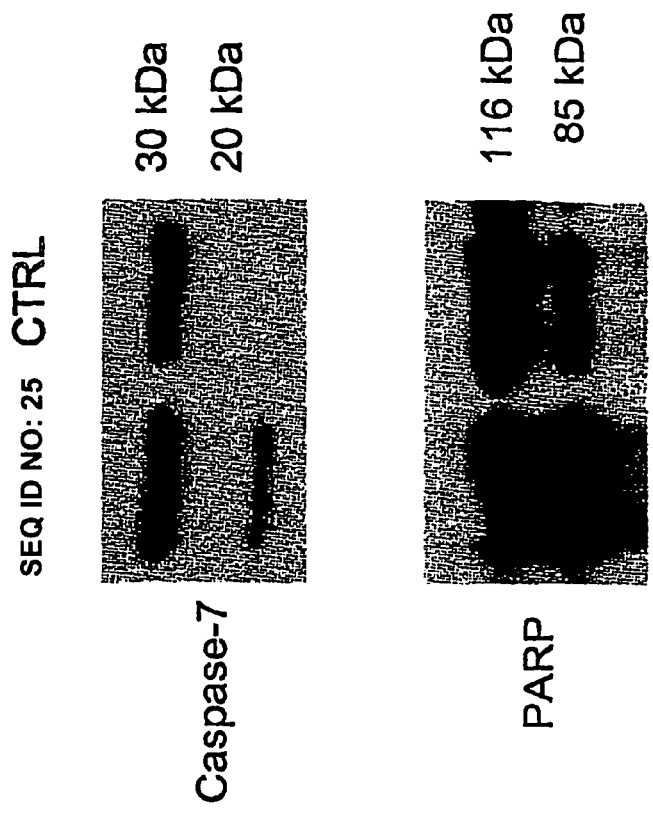
FIG. 3. Caspase activation in Jurkat human T cell leukemia cells. (A) Caspase 3 activation in cells incubated with 0 µg/ml and 100 µg/ml of 6 base GT SEQ ID NO: 25; (B) Caspase 7 activation(a) and PARP content (b) in cells incubated with 0 µg/ml and 100 µg/ml of 6 base GT SEQ ID NO:25.
Figure 3:
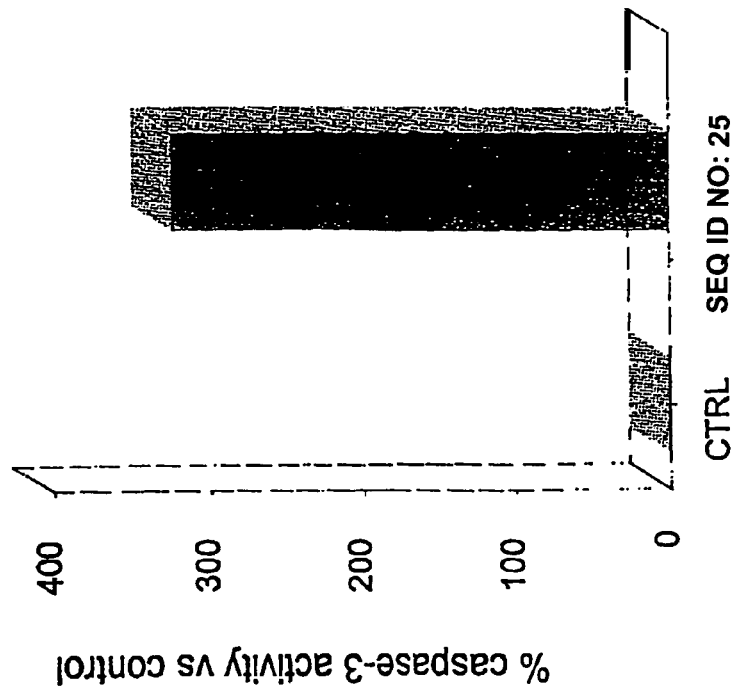

Jurkat T cell leukemia cells were incubated for 72 h with 6 base GT SEQ ID NO:25. Caspase 3 activation was determined calorimetrically as in Example 28. As shown in FIG. 3A, caspase 3 activation in 6 base GT SEQ ID NO:25 treated cells was 323% greater than in control cells.

EXAMPLE 31

Activation of Caspase-7 and PARP Cleavage by GT SEQ ID NO:25

Jurkat T cell leukemia cells were incubated for 72 h with 6 base GT SEQ ID NO:25. The cells were washed 3×with PBS, lysed with 10 mM HEPES, pH 7.5 containing 5 mM $MgCl_2$, 1 mM dithiothreitol, 1.5 nM aprotinin, 10 mM leupeptin and 2.5 μm Na orthovanadate, and the protein content of the lysate was determined (Bradford J. Anal. Biochem. 72:248, 1976).

Activated caspase 7 and PARP cleavage were detected by Western blot analysis. Lysate was mixed with Laemmli buffer (Laemmli U. Nature 15:680, 1970), shaken, and heated at 100° C. for 4 min. Fifty μg of protein was added to each lane and the proteins were separated by electrophoresis in a 10% (caspase) or a 17% (PARP) sodium dodecyl sulfate-polyacrylamide gels (SDS-PAGE) at a constant voltage of 100 V for about 1.5 h. The separated proteins were electroblotted onto a PVDF membrane. Equal protein loading was monitored by Ponceau red staining of the membrane.

The membrane was blocked overnight at 4° C. with a buffer containing 1% Tris-buffered saline (2 mM Tris-HCl, 13.7 mM NaCl, pH 7.6, and 0.1% polyethylenesorbitan monolaurate (TWEEN 20) (TBST) +5% non-fat dry milk. The membrane was washed and was incubated for 1 h at RT with a mouse monoclonal IgG anti-caspase 7 antibody (Pharmingen) (diluted 1:1000 in TBST+1% BSA) or with a mouse monoclonal IgG anti-PARP antibody (diluted 1:1000 in TBST+1% BSA) (Pharmingen). IgG bound to caspase 7 or to PARP was detected with sheep anti-mouse IgG conjugated to horseradish peroxidase (diluted 1:1000 in TBST+ 5% non-fat dry milk) (Pharmingen). Blots were developed using an enhanced chemiluminescence detection system (ECL, Amersham, Corp., Amersham, UK).

As shown in FIG. 3B, 6 base GT SEQ ID NO:25, induced processing of inactive pro-caspase 7 (30 kDa) to active caspase 7 (19–20 kDa) and active PARP to its inactive 85 kDa degradation product.

EXAMPLE 32

Positive Feedback Amplification of Caspase Activation

Jurkat human leukemia T cells are incubated for 72 h with $NH_2$-YVAD-CO-GG(GT)GG, $NH_2$-DEVD-CO-GG(GT) GG, $NH_2$-IEGD-COO-GG(GT)GG, $NH_2$-YVAD-CO-AAC-CACAAGCCCAAC, $NH_2$-DVED-CO-AACCACAAGC-CCAAC and $NH_2$-IEGD-CO-AACCACAAGCCCAAC. Caspase 3 and caspase 7 activation are determined.

$NH_2$-YVAD-CO-GT, $NH_2$-DEVD-CO-GT and $NH_2$-IEGD-COO-GT each induce processing of inactive caspase 3 to active caspase 3 and of inactive caspase 7 to active caspase 7, whereas $NH_2$-YVAD-COACG_3 $NH_2$-DVED-CO-ACG and $NH_2$-IEGD-CO-ACG do not induce processing of inactive pro-caspase 3 to active caspase 3 or of inactive caspase 7 to active caspase 7.

Although not wanting to be bound by the following hypothesis, it is thought that basal caspase activity within caspase containing cells mediates the release of caspase activating GT sequences from NH2-XXXD-COO-GT constructs by proteolysis/hydrolysis. This results in positive amplification of caspase activity (increased levels of caspase 3 and caspase 7) within the cells by the released caspase-activating GT sequences.

EXAMPLE 33

Induction of Cytokine Production

Unless stated otherwise, $1\times10^6$ cells were incubated with 100 μg/ml of each of the sequences tested for 48 h at 37° C. in 5% $CO_2$. Production of cytokines IL-6, IL-10, IL-12, IL-1 beta and TNF-alpha was determined in pg/ml in 100 μl of culture supernatant using the appropriate commercial ELISA (BioSource, Camarillo Calif.). The IL-12 ELISA measures both IL-12 p70 complex and free p40 subunit. Results are expressed as the "fold" (x) increase in cytokine production by treated cells compared to control cells.

THP-1 human acute monocytic leukemia cells were incubated with 2, 3, 6, 9, 12, 14, 15 and 18 base GT sequences and production of the cyotkine IL-6 was determined (Table 35).

TABLE 35

Cytokine production by THP-1 human acute monocytic leukemia cells

| SEQUENCE | ↑IL-6 |
|---|---|
| TG-(TG)$_1$T SEQ ID NO:7-(3 bases) | 2.7× |
| TG-(TG)$_1$ SEQ ID NO:51-(2 bases) | 2.9× |
| TGTGTG-(TG)$_3$ SEQ ID NO:9-(6 bases) | 4.0× |
| GTGTGT-(GT)$_3$ SEQ ID NO:10-(6 bases) | 5.0× |
| TGTGTGTG-(TG)$_4$T SEQ ID NO:11-(9 bases) | 5.4× |
| GTGTGTGTG-(GT)$_4$G SEQ ID NO:12-(9 bases) | 5.4× |
| TGTGTGTGTGT-(TG)$_6$ SEQ ID NO:13-(12 bases) | 5.7× |
| GTGTGTGTGTGT-(GT)$_6$ SEQ ID NO:14-(12 bases) | 1.3× |
| TGTGTGTGTGTGT-(TG)$_7$ SEQ ID NO:15-(14 bases) | 1.0× |
| GTGTGTGTGTGTGTG-(GT)$_7$G SEQ ID NO:16-(15 bases) | 2.6× |
| TGTGTGTGTGTGTGTGT-(TG)$_9$ SEQ ID NO:17-(18 bases) | 2.2× |
| GTGTGTGTGTGTGTGTGT-(GT)$_9$ SEQ ID NO:18-(18 bases) | 2.8× |

As shown in Table 35, 2, 3, 6, 9, 12, 14, 15 and 18 base GT sequences increased THP-1 cell production of the cytokine IL-6.

THP-1 human acute monocytic leukemia cells were incubated with 6 base GT, AG, CG, GG, AGT and CGT sequences and production of the cytokines IL-12 and IL-6 was determined (Table 36).

TABLE 36

Cytokine production by THP-1 human acute monocytic leukemia cells

| SEQUENCE | ↑IL-12 | ↑IL-6 |
|---|---|---|
| TGTGTG-(TG)$_3$ SEQ ID NO:9 | 1.8× | 4.0× |
| GTGTGT-(GT)$_3$ SEQ ID NO:10 | 2.2× | 5.0× |
| TTTGTT-TT(TG)$_1$TT SEQ ID NO:23 | 3.5× | 4.9× |
| GGTGGG-GG(TG)$_1$GG SEQ ID NO:24 | 3.7× | 6.9× |
| GGGTGG-GG(GT)$_1$GG SEQ ID NO:25 | 2.3× | 3.1× |
| TTGTTT-TT(GT)$_1$TT SEQ ID NO:26 | 3.5× | 5.3 |
| AAGTAA-AA(GT)$_1$AA SEQ ID NO:27 | 6.0× | 12.8× |
| CCGTCC-CC(GT)$_1$CC SEQ ID NO:28 | 3.8× | 12.6× |
| TGGTTG-TG(GT)$_1$TG SEQ ID NO:29 | 4.1× | 10.5× |
| ATGTAT-AT(GT)$_1$AT SEQ ID NO:30 | 4.8× | 9.8× |
| AGGTGA-AG(GT)$_1$GA SEQ ID NO:31 | 1.9× | 4.9× |
| GAGTGA-GA(GT)$_1$GA SEQ ID NO:32 | 1.8× | 5.8× |
| GGGTCT-GG(GT)$_1$CT SEQ ID NO:33 | 1.2× | 3.1× |
| CCGTGG-CC(GT)$_1$GG SEQ ID NO:34 | 0.0× | 10.8× |
| GGGTCC-GG(GT)$_1$CC SEQ ID NO:35 | 1.9× | 21.3× |
| CTGTCT-CT(GT)$_1$CT SEQ ID NO:36 | 2.0× | 15.9× |
| TCGTTC-TC(GT)$_1$TC SEQ ID NO:37 | 2.2× | 12.9× |

TABLE 36-continued

Cytokine production by THP-1 human acute monocytic leukemia cells

| SEQUENCE | ↑IL-12 | ↑IL-6 |
|---|---|---|
| CGGTGC-CG(GT)$_1$GC SEQ ID NO:38 | 0.2× | 6.9× |
| TTGTG-TT(GT)$_1$GG SEQ ID NO:39 | 0.0× | 6.6× |
| GGGTT-GG(GT)$_1$TT SEQ ID NO:40 | −1.2× | 14.0× |
| GGTTGG-GG(TT)$_1$GG SEQ ID NO:41 | 3.3× | 16.0× |
| GGAAG-GG(AA)$_1$G SEQ ID NO:42 | 4.1× | 29.2× |
| GGCCGG-GG(CC)GG SEQ ID NO:43 | 3.1× | 17.1× |
| GGGGGG-GG(GG)$_1$GG SEQ ID NO:44 | 0.0× | 15.1× |
| GGGAGG-GG(GA)$_1$GG SEQ ID NO:45 | −1.6× | 23.2× |
| GGGCGG-GG(GC)$_1$GG SEQ ID NO:46 | 2.3× | 9.8× |
| TTAGGG-TT(AG)$_1$GG SEQ ID NO:49 | 2.0× | 6.7× |

As shown in Table 36, 6 base GT, AG, CG, GG, AGT and CGT sequences increased THP-1 cell production of the cytokines IL-12 and IL-6.

Table 37 summarizes the induction of IL-12 and IL-6 synthesis by 6 base sequences.

TABLE 37

IL-6 and IL-12 synthesis induced by 6 base sequences

| Fold increase | IL-12 synthesis SEQ ID NOs: | IL-6 synthesis SEQ ID NOs: |
|---|---|---|
| ≦2.0 | 9, 31, 32, 33, 34, 35, 36, 38, 39, 40, 44, 45, 49 | |
| >2.0 and ≦10.0 | 10, 23, 24, 25, 26, 27, 28, 29, 30, 37, 40, 41, 42, 43, 44, 45 | 9, 10, 23, 24, 25, 26, 30, 31, 32, 33, 38, 39, 46, 49 |
| >10.0 | | 25, 27, 29, 34, 35, 36, 37, 40, 41, 42, 43, 44, 45 |

BCG derived sequences A-3 (SEQ ID NO:73), A-4 (SEQ ID NO:74), A-6 (SEQ ID NO:75), A-7 (SEQ ID NO:76), M3 (SEQ ID NO:77) and Alpha 1 (SEQ ID NO:78) are reported to activate NK cells in vivo (Kataoka et al. Jpn. J. Cancer Res. 83:244, 1992). THP-1 human acute monocytic leukemia cells were incubated with 45 base BCG-derived sequences and production of the cytokines IL-12 and IL-6 was determined (Table 38).

TABLE 38

Cytokine production by THP-1 human acute monocytic leukemia cells

| SEQUENCE | ↑IL-12 | ↑IL-6 |
|---|---|---|
| BCG A-1 AAAGAGGGGCATGACCCGGTGC GGGGCTTCTTGCACTCGGCATAG SEQ ID NO:69-(45 bases) | 1.9× | 2.6× |
| BCG A-2 AAAAGAAGTGGGGTGCCCCCAC GATCACCAACGATGGTGTGTCCA SEQ ID NO:70-(45 bases) | 1.6× | 3.9× |
| BCG A-3 TCCATCGCCAAGGAGATCGAGC TGGAGGATCCGTACGAGAAGATC SEQ ID NO:71-(45 bases) | 1.7× | 2.5× |
| BCG A-4 ACCGATGACGTCGCCGGTGACG GCAACACGACGGCCACCGTGCTG SEQ ID NO:72-(45 bases) | 0.9× | 1.8× |
| BCG A-6 ACGAGACCACCATCGTCGAGGG CGCCGGTGACACCGACGCCATCG SEQ ID NO:73-(45 bases) | 2.1× | 3.9× |
| BCG A-7 GCCGAGAAGGTGCGCAACCTGC CGGCTGGCCACGGACTGAACGCT SEQ ID NO:74-(45 bases) | 0.5× | N.D. |

TABLE 38-continued

Cytokine production by THP-1 human acute monocytic leukemia cells

| SEQUENCE | ↑IL-12 | ↑IL-6 |
|---|---|---|
| BCG M-3 ACGCCGACGTCGTCTGTGGTGG GGTGTCTACCGCCAACGCGACGG SEQ ID NO:75-(45 bases) | 1.6× | 2.8× |
| BCG ALPHA-1 CGACTACAACGGCTGGGATATC AACACCCCGGCGTTCGAGTGGTA SEQ ID NO:76-(45 bases) | 1.1× | 2.1× |

As shown in Table 38, 45 base BCG derived sequences minimally increased THP-1 cell production of IL-12 and IL-6.

EXAMPLE 34

Induction of IL-12 Production by Phosphodiester and Phosphorotothioate Sequences THP-1 human acute monocytic leukemia cells were incubated with 6 base GT sequences, having either an oxygen (phosphodiester) or a sulfur (phosphorothioate) as the nonbridging atom on the phosphate groups and production of the cytokine IL-12 was determined (Table 39).

TABLE 39

IL-12 production by THP-1 human acute monocytic leukemia cells

| | INCREASE | |
|---|---|---|
| SEQUENCE | PHOSPHODIESTER | PHOSPHOROTHIOATE |
| TGTGTG-(TG)$_3$ (6 bases) SEQ ID NO:9 phosphodiester; phosphorothioate | 1.8× | −0.1× |
| GTGTGT-(GT)$_3$ (6 bases) SEQ ID NO:10 phosphodiester; phosphorothioate | 2.2× | −0.2× |
| TTTGT-TT(TG)$_1$TT (6 bases) SEQ ID NO:23 phosphodiester; phosphorothioate | 3.5× | 0.1× |
| GGTGGG-GG(TG)$_1$GG (6 bases) SEQ ID NO:24 phosphodiester; phosphorothioate | 3.7× | −0.1× |
| GGGTGG-GG(GT)$_1$GG (6 bases) SEQ ID NO:25 phosphodiester; phosphorothioate | 2.0× | 0.0× |
| TTGTTT-TT(GT)$_1$TT (6 bases) SEQ ID NO:26 phosphodiester; phosphorothioate | 3.8× | −0.1× |

As shown in Table 39, substitution of a sulfur atom (phosphorothioate) for a nonbridging oxygen atom (phosphodiester) on the phosphate groups resulted in a significant decrease in THP-1 cell production of IL-12.

THP-1 human acute monocytic leukemia cells were incubated with 6 base GT SEQ ID NO:25, having either an oxygen (phosphodiester) or a sulfur (phosphorothioate) as the nonbridging atom on the phosphate groups and production of the cytokine IL-12 was determined (Table 40).

TABLE 40

IL-12 production by THP-1 human acute monocytic leukemia cells

| SEQUENCE* | INCREASE |
|---|---|
| G$_o$G$_o$G$_o$T$_o$G$_o$G$_o$-G$_o$G$_o$(G$_o$T$_o$)$_1$G$_o$G$_o$; (oxygen atom: base 1 to 6) SEQ ID NO:25-(6 bases) | 2.0 |
| G$_o$G$_o$G$_s$T$_o$G$_o$G$_o$-G$_o$G$_o$(G$_s$T$_o$)$_1$G$_o$G$_o$; (oxygen atom: base 1,2,4,5,6; sulfur atom: base 3) SEQ ID NO:25-(6 bases) | 0.1 |

TABLE 40-continued

IL-12 production by THP-1 human acute monocytic leukemia cells

| SEQUENCE* | INCREASE |
|---|---|
| $G_oG_oG_oT_sG_oG_o$-$G_oG_o(G_oT_s)_1G_oG_o$; (oxygen atom: base 1,2,3,5,6; sulfur atom: base 4) SEQ ID NO:25-(6 bases) | 0.2× |
| $G_oG_oG_sT_sG_oG_o$-$G_oG_o(G_sT_s)_1G_oG_o$; (oxygen atom: base 1,2,5,6; sulfur atom: base 3,4) SEQ ID NO:25-(6 bases) | 0.5× |
| $G_sG_oG_oT_oG_oG_s$-$G_sG_o(G_oT_o)_1G_oG_s$; (oxygen atom: base 2,3,4,5; sulfur atom: base 1,6) SEQ ID NO:25-(6 bases) | −0.1× |
| $G_oG_sG_oT_oG_sG_o$-$G_oG_s(G_sT_o)_1G_sG_o$; (oxygen atom: position 1,3,4,6; sulfur atom: position 2,5) SEQ ID NO:25-(6 bases) | −0.1× |
| $G_sG_sG_oT_oG_sG_s$-$G_sG_s(G_oT_o)_1G_sG_s$; (oxygen atom: position 3,4; sulfur atom: position 1,2,5,6) SEQ ID NO:25-(6 bases) | 0 |
| $G_sG_sG_sT_sG_sG_s$-$G_sG_s(G_sT_s)_1G_sG_s$; (sulfur atom: position 1 to 6) SEQ ID NO:25(6 bases) | 0 |

*Note:
"o" represents an oxygen atom and "s" represents a sulfur atom on the phosphate group As shown in Table 40, substitution of a sulfur atom (phosphorothioate) for a nonbridging oxygen atom (phosphodiester) in 6 base GT SEQ ID NO:25 resulted in a significant decrease in THP-1 cell production of IL-12.

EXAMPLE 35

Stimulation of Cytokine Synthesis in Human Peripheral Blood Mononuclear Cells

Peripheral blood mononuclear cells (hereinafter, "PBMCs") were isolated from 7 healthy humans by Ficoll-Hypaque (Amersham Pharmacia Biotech, Baie d'Urfée, Québec, Canada) by density gradient centrifugation of whole blood. PBMCs were incubated with 6 base GT, AGT, CGT, AG, CG and GG sequences and production of the cytokines IL-1beta, IL-6, IL-10 and IL-12 were determined.

TABLE 41

Cytokine production by human PBMC

| SEQUENCES | IL-1beta fold increase: mean +/− SD (range) | IL-6 fold increase: mean +/− SD (range) | IL-10 fold increase: mean +/− SD (range) | IL-12 fold increase: mean +/− SD (range) |
|---|---|---|---|---|
| TG(TG)$_1$TG SEQ ID NO: 9-(6 bases) | 1.2 +/− 0.4 (0.8–1.5) | 8.3 +/− 12.8 (1.2–37.0) | 1.0 +/− 0.1 (0.9–1.1) | 2.7 +/− 2.6 (1.0–6.6) |
| GT(GT)$_1$GT SEQ ID NO: 10-(6 bases) | 2.0 +/− 1.6 (0.9–3.8) | 9.8 +/− 14.2 (0.8–39.1) | 1.0 +/− 0.1 (0.9–1.1) | 4.0 +/− 6.3 (0.9–18.1) |
| TG(TG)$_4$TG SEQ ID NO: 13-(12 bases) | 2.4 +/− 1.9 (0.9–4.5) | 12.1 +/− 6.5 (2.9–20.8) | 1.2 +/− 0.4 (0.9–1.9) | 4.4 +/− 5.3 (1.2–15.0) |
| GT(GT)$_4$GT SEQ ID NO: 14-(12 bases) | 1.1 +/− 0.2 (0.9–1.3) | 2.0 +/− 1.5 (0.9–4.9) | 1.0 +/− 0.1 (0.9–1.2) | 2.0 +/− 1.1 (0.9–2.6) |
| TT(TG)$_1$TT SEQ ID NO: 23-(6 bases) | 1.0 +/− 0.1 (0.9–1.0) | 11.8 +/− 9.0 (1.3–25.6) | 1.0 +/− 0.1 (0.9–1.1) | 1.1 +/− 0.3 (0.9–1.6) |
| GG(TG)$_1$GG SEQ ID NO. 24 (6 bases) | 0.9 +/− 0.1 (0.9–1.0) | 15.9 +/− 14.9 (0.7–37.1) | 2.4 +/− 2.9 (1.0–7.5) | 2.3 +/− 1.6 (0.9–5.5) |
| GG(GT)$_1$GG SEQ ID NO: 25-(6 bases) | 1.0 +/− 0.1 (1.0–1.2) | 20.9 +/− 18.0 (1.6–50.0) | 11.6 +/− 1.2 (9.9–13.2) | 13.2 +/− 11.5 (1.0–26.8) |
| TT(GT)$_1$TT SEQ ID NO: 26-(6 bases) | 1.5 +/− 0.9 (0.9–2.5) | 5.8 +/− 8.0 (0.5–21.7) | 1.0 +/− 0.1 (0.9–1.1) | 1.6 +/− 1.3 (0.8–4.5) |
| AA(GT)$_1$AA SEQ ID NO: 27-(6 bases) | 1.3 +/− 0.5 (0.9–1.8) | 9.6 +/− 7.3 (1.8–16.0) | 1.0 +/− 0.1 (0.9–1.1) | 2.4 +/− 2.2 (0.8–6.7) |
| CC(GT)$_1$CC SEQ ID NO: 28-(6 bases) | 2.1 +/− 1.8 (0.8–4.1) | 10.4 +/− 13.0 (1.4–35.8) | 1.0 +/− 0.1 (1.0–1.1) | 5.9 +/− 10.7 (0.9–30.0) |
| TG(GT)$_1$TG SEQ ID NO: 29-(6 bases) | 1.7 +/− 1.0 (1.1–2.8) | 9.3 +/− 12.1 (0.8–33.8) | 1.0 +/− 0.1 (1.0–1.1) | 3.3 +/− 4.2 (0.8–12.7) |
| AT (GT)$_1$AT SEQ ID NO: 30-(6 bases) | 1.1 +/− 0.2 (1.0–1.4) | 4.6 +/− 4.4 (1.6–14.4) | 1.0 +/− 0.1 (0.9–1.1) | 1.3 +/− 0.2 (1.0–1.6) |
| CT(GT)$_1$CT SEQ ID NO: 36-(6 bases) | 1.2 +/− 0.3 (1.0–1.5) | 5.3 +/− 3.6 (0.9–10.6) | 1.0 +/− 0.1 (0.9–1.2) | 1.2 +/− 0.3 (0.9–1.8) |
| TC(GT)$_1$TC SEQ ID NO: 37-(6 bases) | 1.2 +/− 0.4 (0.9–1.6) | 7.5 +/− 9.8 (0.7–27.0) | 1.0 +/− 0.1 (1.0–1.1) | 1.4 +/− 1.1 (0.9–3.8) |
| GG(TT)$_1$GG SEQ ID NO: 41-(6 bases) | 3.2 +/− 3.0 (0.8–6.5) | 7.8 +/− 12.8 (0.9–36.4) | 1.0 +/− 0.1 (0.9–1.1) | 4.9 +/− 8.6 (0.8–24.3) |
| GG(AA)$_1$GG SEQ ID NO: 42-(6 bases) | 3.5 +/− 3.9 (0.8–8.0) | 11.8 +/− 5.8 (1.2–15.6) | 1.1 +/− 0.2 (0.9–1.5) | 3.0 +/− 2.7 (1.1–8.6) |
| GG(CC)$_1$GG SEQ ID NO: 43-(6 bases) | 1.5 +/− 0.9 (0.8–2.5) | 14.9 +/− 10.2 (1.2–29.8) | 1.2 +/− 0.3 (1.0–1.8) | 2.5 +/− 2.0 (1.0–7.0) |
| GG(GG)$_1$GG SEQ ID NO: 44-(6 bases) | 7.1 +/− 9.4 (0.8–17.9) | 21.0 +/− 14.7 (4.6–42.0) | 1.7 +/− 1.6 (0.9–4.6) | 7.0 +/− 12.5 (1.3–35.3) |
| GG(GA)$_1$GG SEQ ID NO: 45-(6 bases) | 13.6 +/− 14.9 (1.2–30.2) | 24.7 +/− 16.5 (5.9–50.0) | 6.0 +/− 5.5 (2.1–15.5) | 20.7 +/− 10.3 (5.7–35.3) |
| GG(GC)$_1$GG SEQ ID NO: 46-(6 bases) | 1.2 +/− 0.3 (1.0–1.5) | 15.8 +/− 16.2 (1.3–37.8) | 1.0 +/− 0.1 (0.9–1.1) | 3.0 +/− 3.8 (1.1–10.7) |

As shown in Table 41, 6 base GT, AGT, CGT, AG, CG and GG sequences increased human PBMC cell production of the cytokines IL-1 beta, IL-6, IL-10 and IL-12.

EXAMPLE 36

Cytokine Synthesis by Chimpanzee Peripheral Blood Mononuclear Cells

PBMCs were isolated from 4 healthy chimpanzees as in Example 35. Chimpanzee PBMCs were incubated with 6 base GT, AGT, CGT, AG, CG and GG sequences and production of the cytokines IL-10, IL-12 and TNF-alpha was determined (Table 41).

TABLE 41

Cytokine production by chimpanzees PBMC

| SEQUENCES | IL-10 fold increase: mean +/− SD (range) | IL-12 fold increase: mean +/− SD (range) | TNF-alpha fold increase: mean +/− SD (range) |
|---|---|---|---|
| $TG(TG)_1TG$ SEQ ID NO:9- (6 bases) | 2.3 +/− 1.3 (1.3–4.1) | 13.5 +/− 8.9 (2.8–21.1) | 11.3 +/− 6.9 (5.3–19.5) |
| $GT(GT)_1GT$ SEQ ID NO:1- (6 bases) | 4.0 +/− 2.1 (1.8–6.7) | 14.0 +/− 8.5 (3.0–21.3) | 12.9 +/− 6.4 (6.5–19.6) |
| $TT(TG)_1TT$ SEQ ID NO:23- (6 bases) | 1.5 +/− 0.6 (1.0–2.4) | 12.9 +/− 8.2 (2.7–20.1) | 9.0 +/− 5.5 (4.1–14.4) |
| $GG(TG)_1GG$ SEQ ID NO:24- (6 bases) | 2.9 +/− 1.5 (1.3–4.8) | 14.3 +/− 9.1 (3.0–22.5) | 11.9 +/− 7.0 (5.8–19.8) |
| $GG(GT)_1GG$ SEQ ID NO:25- (6 bases) | 2.5 +/− 1.5 (1.4–4.6) | 13.5 +/− 8.4 (2.8–20.8) | 11.7 +/− 6.7 (5.9–19.6) |
| $TT(GT)_1TT$ SEQ ID NO:26- (6 bases) | 1.4 +/− 0.9 (1.1–2.1) | 12.3 +/− 8.5 (2.5–20.1) | 7.5 +/− 4.6 (3.4–13.1) |
| $AA(GT)_1AA$ SEQ ID NO:27 (6 bases) | 2.1 +/− 1.1 (1.1–3.7) | 13.2 +/− 8.2 (2.8–19.8) | 7.9 +/− 3.9 (4.6–12.0) |
| $CC(GT)_1CC$ SEQ ID NO:28- (6 bases) | 3.8 +/− 2.8 (1.5–7.7) | 13.3 +/− 8.4 (2.8–20.4) | 10.3 +/− 5.7 (5.0–15.8) |
| $TG(GT)_1TG$ SEQ ID NO:29- (6 bases) | 3.1 +/− 2.0 (1.6–5.9) | 13.6 +/− 8.8 (2.9–21.9) | 12.4 +/− 7.3 (6.1–20.8) |
| $AT(GT)_1AT$ SEQ ID NO:30- (6 bases) | 1.4 +/− 0.4 (1.2–1.9) | 10.7 +/− 7.0 (2.5–18.6) | 5.9 +/− 3.3 (3.4–10.5) |
| $CT(GT)_1CT$ SEQ ID NO:36- (6 bases) | 3.0 +/− 2.1 (1.2–5.9) | 13.4 +/− 8.9 (2.8–20.4) | 12.4 +/− 6.3 (7.0–19.6) |
| $TC(GT)_1TC$ SEQ ID NO:37- (6 bases) | 3.4 +/− 2.6 (1.4–7.1) | 14.1 +/− 10.0 (2.4–24.9) | 11.4 +/− 6.4 (6.1–19.3) |
| $GG(TT)_1GG$ SEQ ID NO:41 (6 bases) | 9.1 +/− 7.7 (3.0–20.3) | 15.3 +/− 10.0 (2.9–25.9) | 14.1 +/− 7.3 (7.7 +/− 23.2) |
| $GG(AA)_1GG$ SEQ ID NO:42- (6 bases) | 9.9 +/− 8.9 (2.6–22.7) | 15.6 +/− 10.6 (2.6–26.6) | 14.4 +/− 7.1 (8.0–22.9) |
| $GG(CC)_1GG$ SEQ ID NO:43- (6 bases) | 13.6 +/− 9.0 (4.3–26.7) | 15.1 +/− 10.2 (2.8–26.1) | 14.0 +/− 6.6 (7.9–22.3) |
| $GG(GG)_1GG$ SEQ ID NO:44- (6 bases) | 11.2 +/− 9.1 (3.9–24.3) | 15.1 +/− 10.0 (2.9–25.9) | 13.8 +/− 6.5 (7.6–21.8) |
| $GG(GA)_1GG$ SEQ ID NO:45- (6 bases) | 9.9 +/− 9.2 (2.6–23.1) | 15.9 +/− 10.7 (2.9–26.9) | 14.5 +/− 6.9 (7.9–23.0) |
| $GG(GC)_1GG$ SEQ ID NO:46- (6 bases) | 4.7 +/− 3.4 (1.7–9.3) | 15.8 +/− 10.4 (3.0–26.2) | 14.1 +/− 6.6 (8.3–21.7) |

As shown in Table 41, 6 base GT, AGT, CGT, AG, CG and GG sequences increased chimpanzee PBMC cell production of the cytokines IL-10 and IL-12 and TNF-alpha.

EXAMPLE 37

Cytokine Synthesis by Rhesus Monkey Peripheral Blood Mononuclear Cells

PBMCs were isolated from 4 healthy rhesus monkeys as in Example 35. PBMCs were incubated with 6 base GT, AGT, CGT, AG, CG ands GG sequences and production of the cytokines IL-6, IL-12 and TNF-alpha was determined (Table 42).

TABLE 42

Cytokine production by rhesus monkeys PBMC

| SEQUENCES | IL-10 fold increase: mean +/− SD (range) | IL-12 fold increase: mean +/− SD (range) | TNF-alpha fold increase: mean +/− SD (range) |
|---|---|---|---|
| $TG(TG)_1TG$ SEQ ID NO:9- (6 bases) | 1.1 +/− 0.2 (0.9–1.3) | 10.6 +/− 4.2 (5.6–14.3) | 14.3 +/− 6.3 (6.2–21.2) |
| $GT(GT)_1GT$ SEQ ID NO:10- (6 bases) | 1.3 +/− 0.1 (1.1–1.4) | 10.7 +/− 4.1 (6.1–15.8) | 16.1 +/− 4.2 (11.0–21.6) |
| $TT(TG)_1TT$ SEQ ID NO:23- (6 bases) | 1.0 +/− 0.1 (0.8–1.0) | 6.7 +/− 3.6 (3.6–11.7) | 4.4 +/− 3.8 (1.3–9.5) |
| $GG(TG)_1GG$ SEQ ID NO:24- (6 bases) | 1.0 +/− 0.1 (1.0–1.1) | 11.2 +/− 4.8 (5.6–16.8) | 14.5 +/− 5.4 (7.7–20.0) |
| $GG(GT)_1GG$ SEQ ID NO:25- (6 bases) | 1.0 +/− 0.1 (1.0–1.1) | 10.6 +/− 4.7 (5.5–16.5) | 12.5 +/− 5.2 (6.2–18.6) |
| $TT(GT)_1TT$ SEQ ID NO:26- (6 bases) | 1.0 +/− 0.1 (1.0–1.2) | 4.9 +/− 2.9 (2.6–8.8) | 2.1 +/− 1.0 (1.3–3.4) |
| $AA(GT)_1AA$ SEQ ID NO:27- (6 bases) | 0.9 +/− 0.1 (0.9–1.0) | 7.6 +/− 2.6 (5.9–11.5) | 6.0 +/− 5.0 (2.4–13.4) |
| $CC(GT)_1CC$ SEQ ID NO:28- (6 bases) | 1.1 +/− 0.2 (0.9–1.2) | 10.1 +/− 3.7 (6.2–14.2) | 14.2 +/− 3.7 (9.6–18.6) |
| $TG(GT)_1TG$ SEQ ID NO:29- (6 bases) | 1.1 +/− 0.2 (0.9–1.2) | 11.1 +/− 4.2 (6.5–15.7) | 16.5 +/− 2.7 (14.0–19.1) |
| $AT(GT)_1AT$ SEQ ID NO:30- (6 bases) | 1.9 +/− 1.4 (1.0–4.0) | 6.0 +/− 1.9 (5.6–8.5) | 6.9 +/− 4.7 (2.2–13.4) |
| $CT(GT)_1CT$ SEQ ID NO:36- (6 bases) | 1.0 +/− 0.1 (0.9–1.1) | 10.7 +/− 4.6 (6.2–16.4) | 15.3 +/− 3.6 (11.2–19.8) |
| $TC(GT)_1TC$ SEQ ID NO:37- (6 bases) | 1.1 +/− 0.2 (0.9–1.3) | 10.0 +/− 3.8 (6.3–14.1) | 14.7 +/− 3.1 (13.7–19.1) |
| $GG(TT)_1GG$ SEQ ID NO:41- (6 bases) | 1.9 +/− 1.5 (1.0–4.1) | 11.5 +/− 5.9 (4.3–17.2) | 14.1 +/− 8.2 (2.5–20.7) |
| $GG(AA)_1GG$ SEQ ID NO:42- (6 bases) | 1.2 +/− 0.2 (1.0–1.4) | 11.9 +/− 5.4 (5.9–17.1) | 16.5 +/− 4.5 (11.4–21.2) |
| $GG(CC)_1GG$ SEQ ID NO:43- (6 bases) | 1.0 +/− 0.2 (0.8–1.2) | 11.7 +/− 4.8 (6.2–16.4) | 16.9 +/− 3.5 (13.9–21.1) |
| $GG(GG)_1GG$ SEQ ID NO:44- (6 bases) | 2.1 +/− 1.0 (1.1–3.5) | 10.7 +/− 5.6 (3.7–15.9) | 13.9 +/− 8.5 (2.0–20.9) |
| $GG(GA)_1GG$ SEQ ID NO:45- (6 bases) | 1.1 +/− 0.1 (1.0–1.3) | 11.9 +/− 4.5 (6.8–16.0) | 16.7 +/− 4.6 (11.6–21.5) |
| $GG(GC)_1GG$ SEQ ID NO:46- (6 bases) | 1.2 +/− 0.2 (1.0–1.4) | 11.0 +/− 4.4 (6.3–16.1) | 16.8 +/− 4.1 (11.9–21.8) |

As shown in Table 42, 6 base GT, AGT, CGT, AG, CG and GG sequences increased rhesus monkey PBMC cell production of the cytokines IL-10, IL-12 and TNF-alpha.

EXAMPLE 38

Effect of 6 Base GT SEQ ID NO:25 of 6 Base GT SEQ ID NO:25+5-fluorouracil and of 6 Base GT SEQ ID NO:25+ Tamoxifen on MCF-7 Human Breast Tumors MCF-7 human breast cancer cells are implanted subcutaneously as xenografts, in female nude BALB/c mice. The mice are divided into 6 groups of 10 mice. On day 0, group 1 mice receive saline, group 2 mice receive 6 base GT SEQ ID NO:25, group 3 mice receive receive 5-fluorouracil, group 4 mice receive tamoxifen, group 5 mice receive 6 base GT SEQ ID NO:25+5-fluorouracil and group 6 mice receive 6 base GT SEQ ID NO:25+tamoxifen. After 4 weeks of treatment, the mice are sacrificed and tumor mass is determined. Group 1 mice have the most tumor mass, groups 2, 3 and 4 mice have less tumor mass than group 1 mice and groups 5 and 6 mice have less tumor mass than groups 1, 2, 3 and 4 mice.

EXAMPLE 39

Effect of 3 and 6 Base GT Sequences and 45 Base BCG A-3 Sequence on LNCaP Human Prostate Cancer Tumors LNCaP human prostate cancer cells are implanted subcutaneously, as xenografts, in male nude nu/nu mice. The mice are divided into 5 groups of 10 mice. On day 0, group 1 mice receive saline, group 2 mice receive 3 base SEQ ID NO:8, group 3 mice receive 6 base GT SEQ ID NO:25, group 4 mice receive 6 base AG SEQ ID NO:45 and group 5 mice receive 45 base BCG A-3 SEQ ID NO:69. After 4 weeks of treatment, the mice are sacrificed and tumor mass is determined. Group 1 mice have the most tumor mass, group 5 mice have less tumor mass than group 1 mice and groups 2, 3 and 4 mice have less tumor mass than groups 1 and 5 mice.

EXAMPLE 41

Effect of 3, 6, 8 and 27 Base Sequences on EL-4 Murine T Lymphomas

EL-4 murine T lymphoma cells are implanted into C57/BL6 mice. The mice are divided into 6 groups of 10 mice. On day 0, group 1 mice receive saline, group 2 mice receive 3 base GT SEQ ID NO:8, group 3 mice receive 6 base SEQ ID NO:25, group 4 mice receive 6 base AG SEQ ID NO:45, group 5 mice receive 18 base GT SEQ ID NO:18 and group 6 mice receive 27 base GT SEQ ID NO:1. After 4 weeks of treatment, the mice are sacrificed and tumor mass is determined. Group 1 mice have the most tumor mass, groups 2, 3, 4, 5 and 6 mice have less tumor mass than group 1 mice.

EXAMPLE 42

Human colon cancer cell lines are maintained as adherent cell cultures. Cells in the exponential growth phase are treated with 2–20 base GT, GA, GC or GG sequences in the dose range 0 µg/ml to 100 µl/ml for 24–72 hours. Inhibition of cell proliferation is measured by MTT reduction, cell cycle arrest by flow cytometry and apoptosis by annexin-V binding or NuMA release. GT, GA, GC or GG sequences inhibit proliferation, induce cell cycle arrest and induce apoptosis in the colon cancer cell lines.

SCID mice bearing subcutaneous human colorectal cancer cell lines are treated with saline or with 2–20 base GT, GA, GC or GG sequences, having anti-cancer activity against human colorectal cancer cell lines in vitro Mice treated with 2–20 base GT, GA, GC or GG sequences, having anti-cancer activity against human colorectal cancer cell lines in vitro, show a significant reduction in tumor mass compared with mice treated with saline.

While the invention has been described in detail and with reference to specific embodiments thereof, it will be apparent to one skilled in the art that various changes and modifications can be made therein without departing from the spirit and scope thereof.

---

We claim:

1. A composition comprising a 3'-OH, 5'-OH synthetic phosphodiester nucleotide sequence, a chemotherapeutic agent, and a pharmaceutically acceptable carrier, wherein the synthetic phosphodiester nucleotide sequence is selected from the group consisting of SEQ ID NOs:8–10, 25, 26, 41–43, 45 and 46.

2. The composition of claim 1, wherein the chemotherapeutic agent is an antimetabolite, an alkylating agent, or a hormone antagonist.

3. The composition of claim 1, wherein the synthetic phosphodiester nucleotide sequence is SEQ ID NO:8.

4. The composition of claim 1, wherein the synthetic phosphodiester nucleotide sequence is SEQ ID NO:10.

5. The composition of claim 1, wherein the synthetic phosphodiester nucleotide sequence is SEQ ID NO:25.

6. The composition of claim 1, wherein the synthetic phosphodiester nucleotide sequence is SEQ ID NO:42.

7. The composition of claim 1, wherein the synthetic phosphodiester nucleotide sequence is SEQ ID NO:43.

8. The composition of claim 1, wherein the synthetic phosphodiester nucleotide sequence is SEQ ID NO:45.

9. A composition comprising a 3'-OH, 5'-OH synthetic phosphodiester nucleotide sequence, a chemotherapeutic agent, and a pharmaceutically acceptable cater, wherein the synthetic phosphodiester nucleotide sequence is selected from the group consisting of SEQ ID NOs:8–10, 25, 26, 41–43, 45 and 46, and the chemotherapeutic agent is an antimetabolite, an alkylating agent, or a hormone antagonist.

10. The composition of claim 9, wherein the synthetic phosphodiester nucleotide sequence is SEQ ID NO:8.

11. The composition of claim 9, wherein the synthetic phosphodiester nucleotide sequence is SEQ ID NO:9.

12. The composition of claim 9, wherein the synthetic phosphodiester nucleotide sequence is SEQ ID NO:10.

13. The composition of claim 9, wherein the synthetic phosphodiester nucleotide sequence is SEQ ID NO:25.

14. The composition of claim 9, wherein the synthetic phosphodiester nucleotide sequence is SEQ ID NO:26.

15. The composition of claim 9, wherein the synthetic phosphodiester nucleotide sequence is SEQ ID NO:41.

16. The composition of claim 9, wherein the synthetic phosphodiester nucleotide sequence is SEQ ID NO:42.

17. The composition of claim 9, wherein the synthetic phosphodiester nucleotide sequence is SEQ ID NO:43.

18. The composition of claim 9, wherein the synthetic phosphodiester nucleotide sequence is SEQ ID NO:45.

19. The composition of claim 9, wherein the synthetic phosphodiester nucleotide sequence is SEQ ID NO:46.

20. The composition of claim 1, wherein the synthetic phosphodiester nucleotide sequence is SEQ ID NO:9.

21. The composition of claim 1, wherein the synthetic phosphodiester nucleotide sequence is SEQ ID NO:26.

22. The composition of claim 1, wherein the synthetic phosphodiester nucleotide sequence is SEQ ID NO:41.

23. The composition of claim 1, wherein the synthetic phosphodiester nucleotide sequence is SEQ ID NO:46.

* * * * *